United States Patent
Suzuki et al.

[11] Patent Number: 5,837,113
[45] Date of Patent: *Nov. 17, 1998

[54] SMALL GLASS ELECTRODE

[75] Inventors: Hiroaki Suzuki; Akio Sugama; Naomi Kojima, all of Kawasaki, Japan

[73] Assignee: Fujitsu Limited, Kawasaki, Japan

[*] Notice: The term of this patent shall not extend beyond the expiration date of Pat. No. 5,417,837.

[21] Appl. No.: 598,287

[22] Filed: Feb. 8, 1996

Related U.S. Application Data

[63] Continuation of Ser. No. 153,054, Nov. 17, 1993, abandoned, which is a continuation-in-part of Ser. No. 803,433, Dec. 6, 1991, Pat. No. 5,417,837.

[30] Foreign Application Priority Data

| Dec. 6, 1990 | [JP] | Japan | 2-400550 |
|---|---|---|---|
| Jul. 5, 1991 | [JP] | Japan | 3-164750 |
| Nov. 17, 1992 | [JP] | Japan | 4-306847 |
| Mar. 29, 1993 | [JP] | Japan | 5-070328 |

[51] Int. Cl.$^6$ ................................. G01N 27/36
[52] U.S. Cl. .................. 204/420; 65/40; 156/272.2; 156/273.9; 204/435; 216/41; 216/97; 216/99
[58] Field of Search ................... 204/416–420, 204/435

[56] References Cited

U.S. PATENT DOCUMENTS

| 3,458,422 | 7/1969 | Proctor, Jr. ............................ 204/195 |
|---|---|---|
| 3,560,256 | 2/1971 | Abrams ................................. 117/212 |
| 3,676,319 | 7/1972 | Kirsten ............................. 204/195 F |
| 4,139,833 | 2/1979 | Kirsch ................................. 338/308 |
| 4,280,889 | 7/1981 | Szonntagh ............................ 204/420 |
| 4,300,990 | 11/1981 | Maurer ............................ 204/195 S |
| 4,368,453 | 1/1983 | Herden et al. ........................ 338/25 |
| 4,418,329 | 11/1983 | Gruner ................................. 338/28 |
| 4,508,613 | 4/1985 | Busta et al. ........................ 204/420 |
| 4,516,106 | 5/1985 | Nolting et al. ........................ 338/28 |
| 4,592,824 | 6/1986 | Smith et al. ........................ 204/416 |
| 4,691,566 | 9/1987 | Aine ................................. 73/204 |
| 4,786,396 | 11/1988 | Yee et al. ........................ 204/420 |
| 4,816,132 | 3/1989 | Kotani et al. ........................ 204/408 |
| 4,842,712 | 6/1989 | Seshimoto et al. .................. 204/416 |
| 4,874,499 | 10/1989 | Smith et al. ........................ 204/403 |
| 4,888,463 | 12/1989 | Middlebrook ........................ 219/201 |
| 4,888,988 | 12/1989 | Lee et al. ........................ 73/204.26 |
| 4,975,175 | 12/1990 | Karube et al. ........................ 204/403 |
| 5,010,315 | 4/1991 | Fedter et al. ........................ 338/7 |
| 5,183,550 | 2/1993 | Mattiessen ........................ 204/415 |
| 5,417,837 | 5/1995 | Suzuki et al. ........................ 204/420 |

FOREIGN PATENT DOCUMENTS

| 0269031 A2 | 6/1988 | European Pat. Off. . |
|---|---|---|
| 63-015484 | 1/1988 | Japan . |
| 63-164232 | 7/1988 | Japan . |
| 1-262679 | 10/1989 | Japan . |
| 2-263127 | 10/1990 | Japan . |
| 3-131003 | 6/1991 | Japan . |
| 3-204981 | 9/1991 | Japan . |

*Primary Examiner*—T. Tung
*Attorney, Agent, or Firm*—Staas & Halsey

[57] ABSTRACT

A small glass electrode and process for preparation thereof, the small glass electrode having a bonded structure and comprising a reference electrode composed of silver/silver chloride, a glass substrate having a pad embedded therein, the pad being composed of gold or platinum and circuit-connected to the reference electrode, and a silicon substrate having a (100) plane selectively etched by the anisotropic etching technique and comprising a groove for injecting an electrolyte composed of an aqueous solution containing chlorine such as KCA, or HCA, at least one hole for holding the electrolyte and a glass film formed in a portion corresponding to the reference electrode. The structure of the small glass electrode may be produced by the disclosed process easily and at low cost. Additionally, the small glass electrode, in differing embodiments, may include a reference electrode and a temperature sensor.

23 Claims, 21 Drawing Sheets

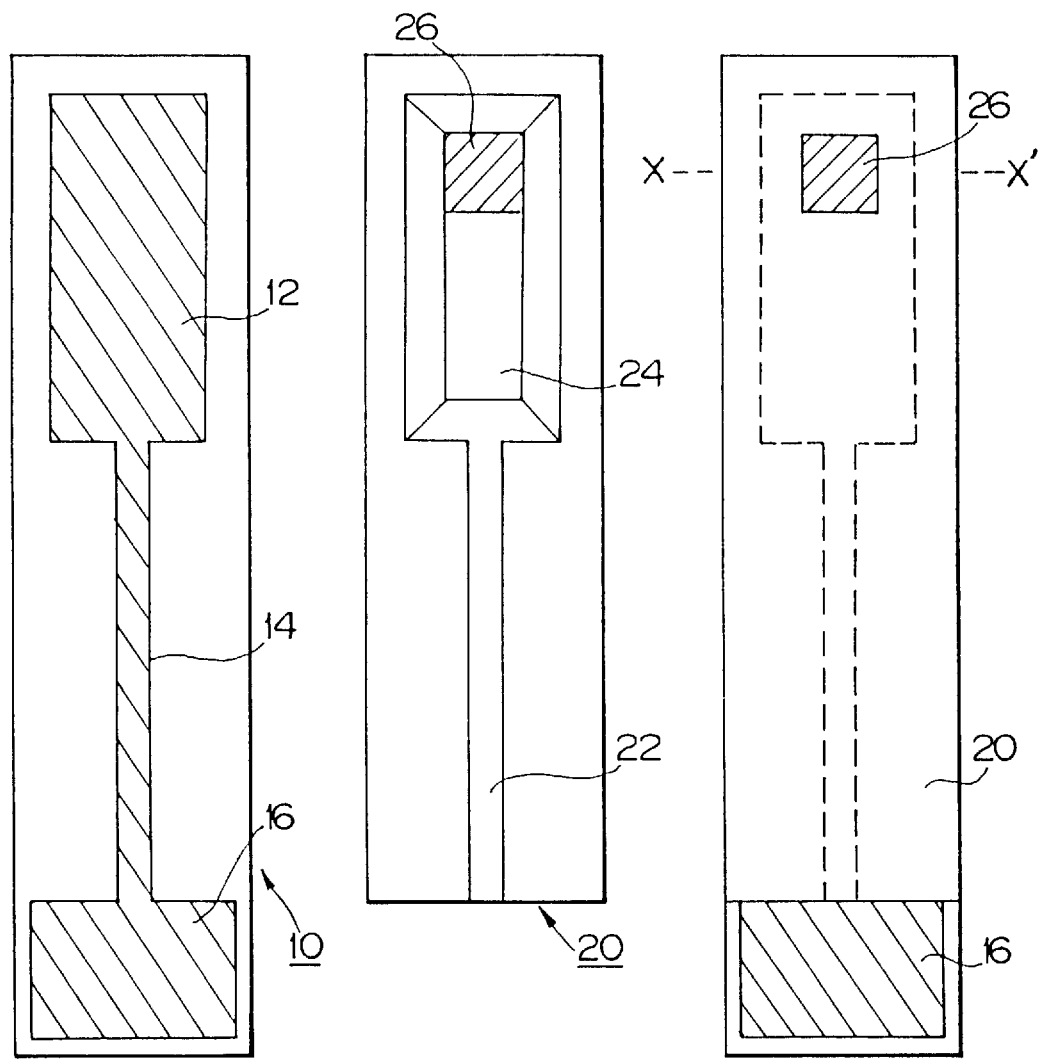

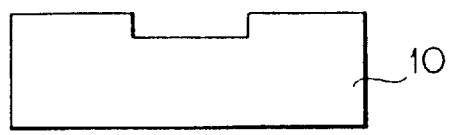
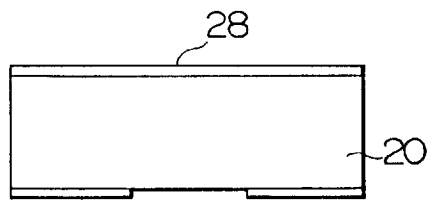
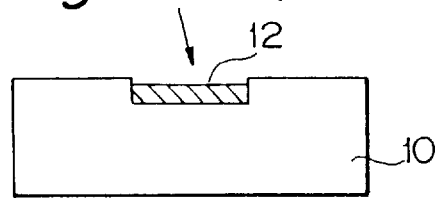
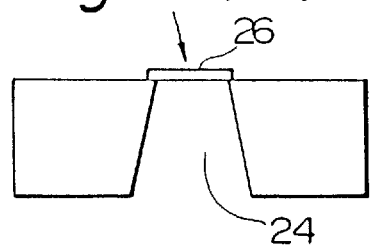
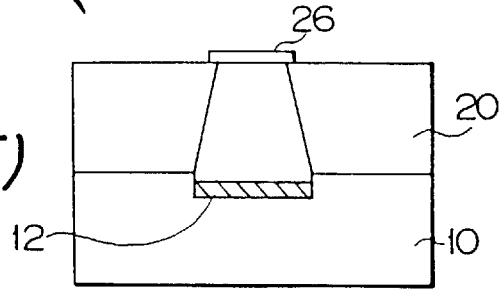
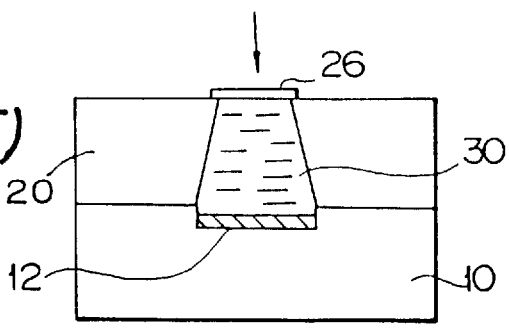

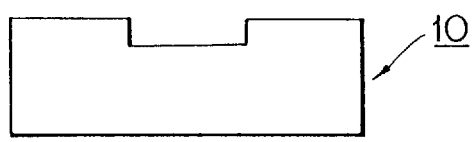
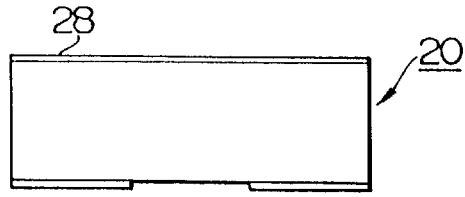
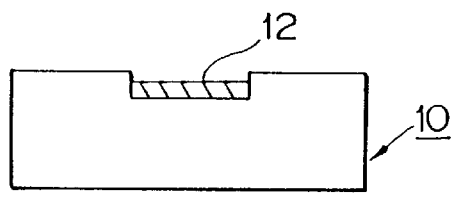
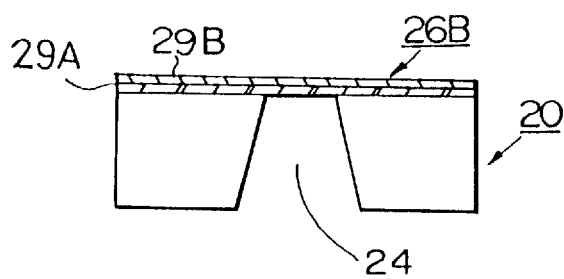
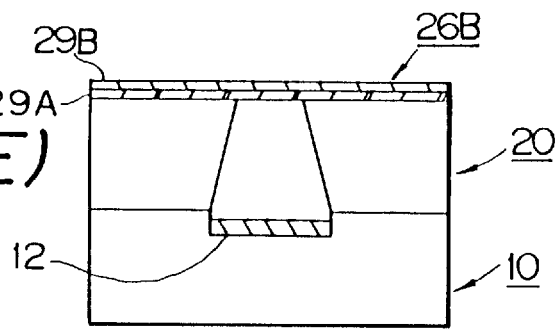
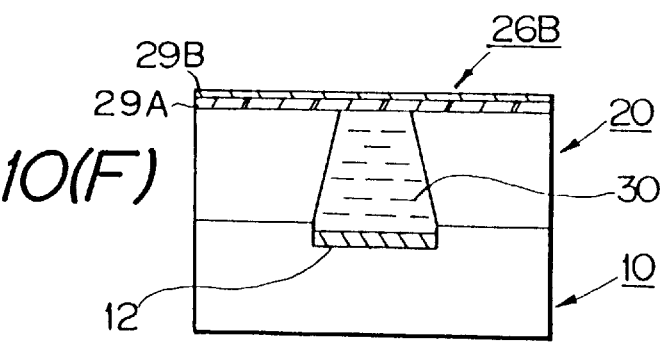

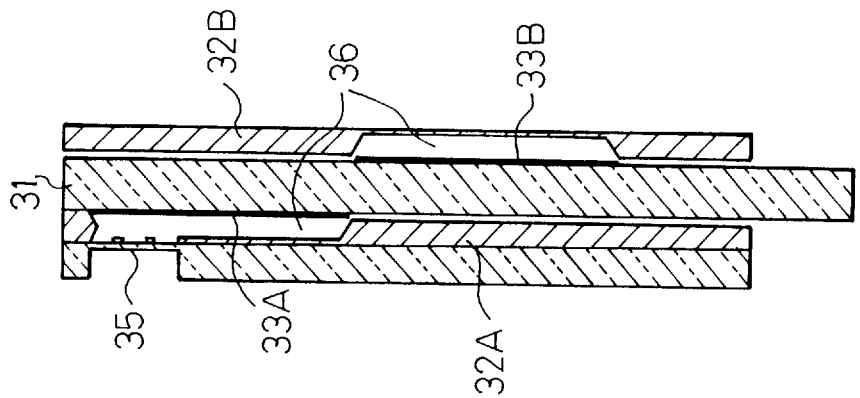
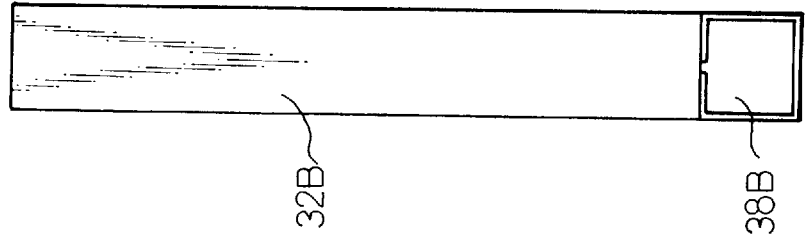
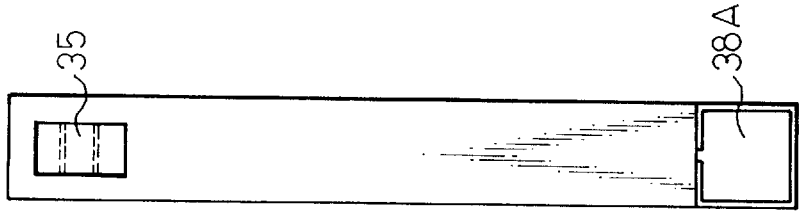

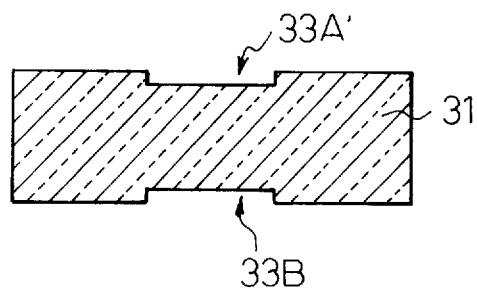
Fig.16A
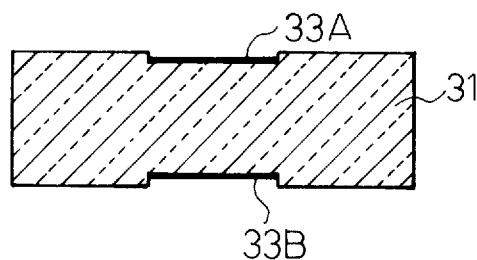
Fig.16B
Fig.16C
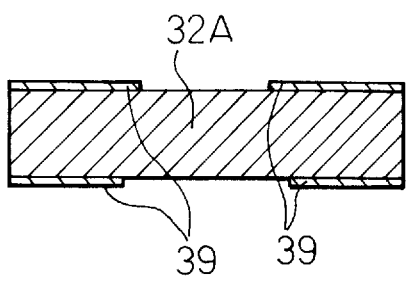
Fig.16D
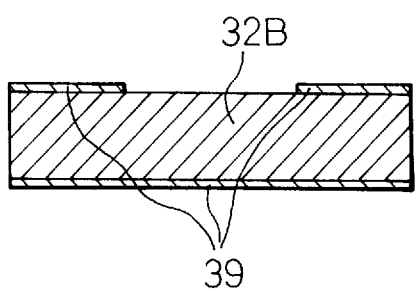
Fig.16E
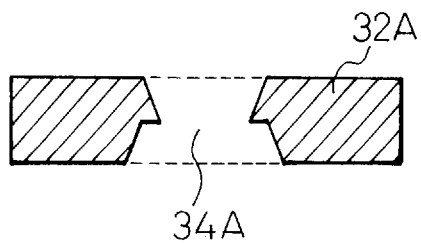
Fig.16F
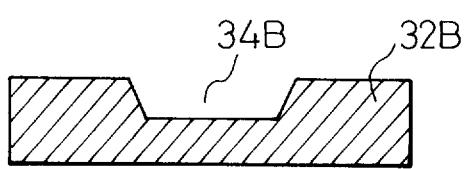

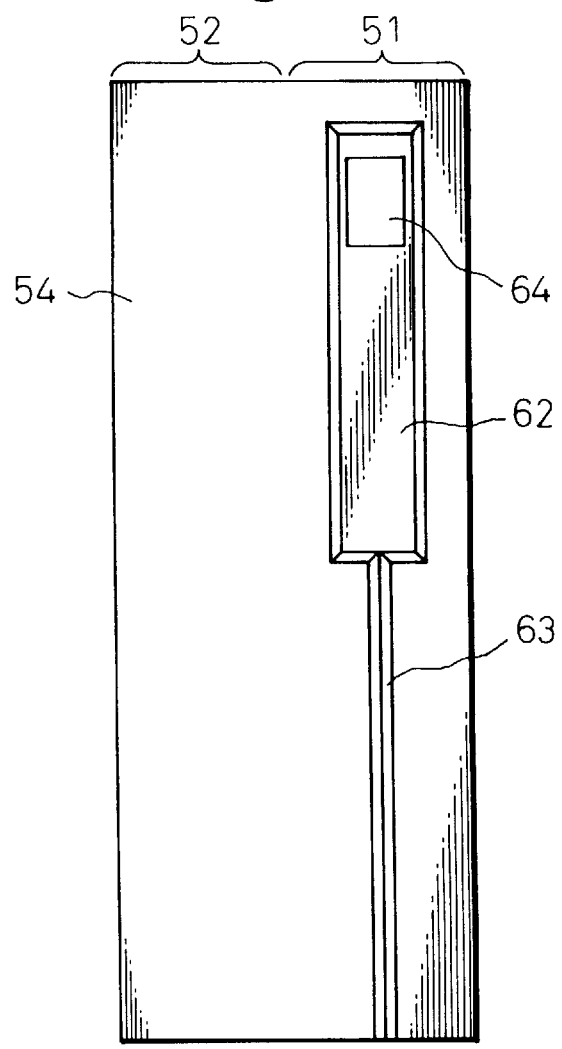

SMALL GLASS ELECTRODE

CROSS-REFERENCE TO RELATED APPLICATION

This application is a continuation, of application Ser. No. 08/153,054, filed Nov. 17, 1993, now abandoned which is a continuation-in-part of U.S. Ser. No. 803,433 filed Dec. 6, 1991 U.S. Pat. No. 5,417,837, issued May 23, 1995.

BACKGROUND OF THE INVENTION (1) Field of the Invention

The present invention relates to a small glass electrode and a process for the preparation thereof. More particularly, the present invention relates to a small glass electrode formed by utilizing a micro-machining technique and a process for the preparation thereof.

(2) Description of the Related Art

A glass electrode is easily usable as a sensor for determining the hydrogen ion ($H^+$) concentration in an aqueous solution, and is widely and generally used.

The determination of the $H^+$ concentration is required not only in ordinary chemical experiments but also in fermentation control and in the medical field.

Furthermore, a biosensor fabricated by combining a glass electrode with either enzymes or microorganisms can be used for determining various chemical compounds.

For example, glucose reacts with dissolved oxygen with the aid of a catalyst called glucose oxidase and is oxidized to gluconolactone. Changes of the $H^+$ concentration during this reaction are measured, and the glucose concentration can be determined from the changed quantities. According to a similar principle, the urea concentration can be determined.

In the glass electrode, the $H^+$ concentration is measured by utilizing the electroconductivity of glass. Namely, the phenomenon that when a glass film having a thickness of about 100 $\mu$m and an electrical resistance of several hundred M$\Omega$ is placed in a solution, a voltage difference is produced according to the pH value of the solution which is utilized.

FIG. 1 illustrates the structure of a sensing portion of a conventional glass electrode, which comprises a reference electrode 2 composed of silver/silver chloride (Ag/AgCl), an internal solution 4 such as a potassium chloride (KCl) solution having a certain concentration, and a spherical sensing glass film 6 formed on the top end.

When this glass electrode is immersed in a solution containing $H^+$, in response to the active quantity (ai) of $H^+$, a potential is generated according to the Nernst equation:

$$E = const + (RT/F) ln\, ai \quad (1)$$

wherein E represents the potential of the glass electrode, R represents the gas constant, T represents the absolute temperature, and F is the Faraday constant.

Accordingly, the $H^+$ concentration is determined by the above equation.

However, the commercially available glass electrode has a size similar to that of a fountain pen, as shown in FIG. 1, and the glass electrode is formed by glazing and it is expensive.

An ion-sensitive electric field effect transistor (abbreviated to "ISFET") has been developed as a small $H^+$ concentration sensor. Since a photo-lithographic technique of semiconductor production is utilized for its formation, the size thereof can be reduced.

In a device immersed in an aqueous solution, such as ISFET, insulation of the substrate is important.

Accordingly, many elements formed on a silicon (Si) substrate are diced into chips and a silicon nitride ($Si_3N_4$) film is formed on the peripheries of the chips to effect insulation, or an SOS (silicon-on-sapphire) substrate is used. Alternatively, there is adopted a method in which a thin film transistor (TFT) is formed on a glass substrate. However, the increased price of such a structure cannot be avoided and therefore, the sensor cannot be manufactured at a low price.

The conventional glass electrode formed by glazing is large size and expensive. In an ISFET formed by the photolithography of an Si substrate, insulation is indispensable and a price increase is inevitably caused by the necessity of maintaining the insulation, and thus, reduction of the price is not easy.

Under this background, development of another method of providing a practical glass electrode of small size and low price is desired.

In addition to the need as explained hereinabove of providing both a structure of and a method for producing a practical glass electrode of small size and low price, it further is desirable to afford such a small glass electrode which includes reference electrodes and eliminates the need of a separate reference electrode as is typical in conventional such devices.

Yet further, it is desirable that, in addition to the foregoing need for a practical glass electrode of small size and low price, relative to those available in the prior art, that such a small glass electrode be provided with a temperature sensor and specifically a temperature sensor which may be responsive to ambient temperatures which affect the exterior of the small glass electrode.

Accordingly, there is a continuing need for a practical glass electrode of small size and low price, relative to those available in the prior art which, moreover, satisfy the foregoing requirements and demands.

SUMMARY OF THE INVENTION

It is an object of the present invention to provide a small glass electrode capable of overcoming the foregoing problems of conventional such devices and a process for the preparation thereof.

Moreover, it is a further object of the present invention to afford a small glass electrode which satisfies these criteria, and a process for the preparation thereof, and which device furthermore satisfies the foregoing additional requirements and demands of such a device incorporating reference electrodes and/or a temperature sensor.

In accordance with one aspect of the present invention, this object can be attained by a small glass electrode, which has a bonded structure comprising a reference electrode composed of silver/silver chloride, a glass substrate having a pad embedded therein, said pad being composed of gold or platinum and which is circuit-connected to the reference electrode, and a silicon substrate having a (100) plane selectively etched by the anisotropic etching technique and comprising a groove for injecting an electrolyte containing chlorine, such as a potassium chloride buffer solution or hydrochloric acid solution, at least one reservoir for holding the electrolyte and a glass film formed in a portion corresponding to the reference electrode.

The glass film may have a multiple-layer (for example, two-layer) structure.

In accordance with another aspect of the present invention, there is provided a process for the preparation of a small glass electrode, which comprises selectively etching a glass substrate, forming a reference electrode, composed of silver/silver chloride and a pad composed of gold or platinum and circuit-connected to the reference electrode, on the etched portion, subjecting a silicon substrate having a (100) plane as the substrate face to anisotropic etching to form an electrolyte-injecting groove and at least one electrolyte-holding reservoir therein, forming a glass film acting as a sensing film by utilizing a silicon oxide film as a mask, and bonding the formed glass substrate and silicon substrate to each other.

In accordance with still another aspect of the present invention, there is provided a process for the preparation of a small glass electrode, which comprises selectively etching a glass substrate, forming a reference electrode, composed of silver/silver chloride and a pad composed of gold or platinum and circuit-connected to the reference electrode, on the etched portion, subjecting a silicon substrate having a (100) plane as the substrate face to anisotropic etching to form an electrolyte-injecting groove and at least one electrolyte-holding reservoir therein, removing the silicon oxide film which remains on the silicon substrate face, forming a glass film acting as a sensing film in a lower portion of the reservoir, and bonding the formed glass substrate and silicon substrate to each other.

The process of the present invention may further comprise a step of injecting the electrolyte into the reservoir from the injecting groove, according to need. Accordingly, a small glass electrode having an electrolyte injected in the reservoir is included within the scope of the present invention.

In accordance with yet another embodiment of the invention, there is afforded a small glass electrode which includes reference electrodes and thus eliminates the need of a separate reference electrode as required for use in combination with conventional such devices and thus rendering the further embodiment more convenient and practical for use than conventional such devices. In accordance with this further embodiment of the small glass electrode of the invention, the latter comprises a planar insulating substrate including an inside reference electrode formed on a first surface of the insulating substrate and an outside reference electrode formed on a second surface of the insulating substrate, a first silicon substrate bonded onto the insulating substrate, the first silicon substrate having a first dent portion which covers the inside reference electrode and a penetrating hole formed in a portion of the first dent portion, the penetrating hole being covered by a glass sensing film bonded onto the first silicon substrate, the first dent portion forming a storage for an electrolyte, a second silicon substrate bonded onto the insulating substrate, the second silicon substrate having a second dent portion which covers the outside reference electrode and communicates with the exterior through a salt bridge, the second recess portion forming a storage for an electrolyte, and an electrolyte filled in the first and second dent portions.

In accordance with yet a further embodiment of the invention, a small glass electrode in accordance with the foregoing is provided with a temperature sensor, and which may take into account the effect on the outside of the small glass electrode of ambient temperature. In accordance with this embodiment of the invention, the small glass electrode is combined with a temperature sensor and comprises first and second substrates directly bonded to each other, the bonded substrates having a first portion for a glass electrode and a second portion for a temperature electrode, the first and second portions being separated from each other. Further, the first portion comprises a reference electrode formed on the first substrate, a dent formed on the second substrate for confronting the reference electrode and holding an electrolyte, a groove formed on the second substrate for injecting an electrolyte into the hole and a glass film formed on the second substrate for covering at least a portion of the hole at a portion corresponding to the reference electrode, and wherein the second portion further comprises a thin film resistor formed between the bonded first and second substrates in the second portion.

BRIEF DESCRIPTION OF THE DRAWINGS

Objects as well as advantages of the present invention will be come clear from the following description of the preferred embodiments made with reference to the accompanying drawings, wherein:

FIG. 2(A) is a planar view of a glass substrate of the glass electrode according to one embodiment of the present invention, FIG. 2(B) is a planar view of an Si substrate of the glass electrode according to this embodiment, and FIG. 2(C) is a planar view of the glass electrode of this embodiment of the present invention, formed by bonding the glass substrate and Si substrate shown in FIGS. 2(A) and 2(B);

FIGS. 4(A) to 4(F) are diagrams illustrating steps of forming the glass electrode according to one embodiment of the present invention;

FIGS. 10(A) to 10(F) are diagrams illustrating steps of forming the glass electrode according to still another embodiment of the present invention;

FIGS. 13A to 13C are front and rear plan views and a cross-sectional view of a small glass electrode in accordance with the second embodiment of the invention and which includes reference electrodes;

FIGS. 17A to 17C show a small glass electrode provided with a temperature sensor in accordance with a second embodiment of the present invention, wherein FIG. 17A is a plan view of the glass electrode and FIGS. 17B and 17C are plan views of the two substrates of the glass electrode.

DETAILED DESCRIPTION OF THE PREFERRED EMBODIMENTS

Figure 1:
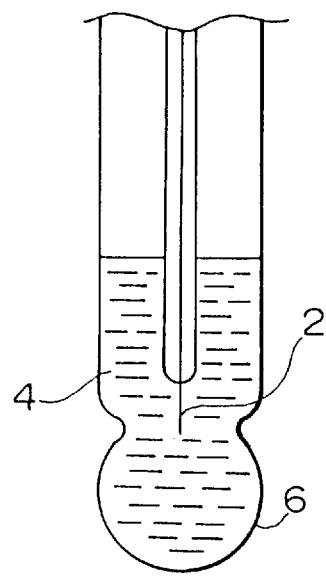
FIG. 1 is a cross-sectional view of a conventional glass electrode.

The present inventors already succeeded in providing a practical utilizable small Clark oxygen electrode by applying the micro-machining technique to an Si substrate (USP 4975175).

This small oxygen electrode is often used for medical treatment. In this case, the oxygen concentration is measured relative to the $H^+$ concentration, rather than the oxygen concentration alone.

Accordingly, practical utilization of a small glass electrode by using the micro-machining technique was tried.

The following plan describes said utilization by the present inventors:

(1) The size of the glass electrode, presently used as the $H^+$ concentration sensor and found to operate well, is reduced.

(2) At least one holding hole (i.e., a cavity or reservoir) formed by anisotropic etching of an Si substrate, is used as a vessel for storing an electrolyte.

(3) A glass film formed by heat oxidation or sputtering is used as a sensing film (sensing element) for responding to the $H^+$ concentration.

(4) A reference electrode is formed on a glass substrate, and the glass substrate and Si substrate are bonded and integrated by the anodic bonding method.

(5) A reference electrode composed of Ag/AgCl, a lead-in line and a pad are embedded in the glass substrate.

The glass substrate to be bonded to the Si substrate is required to adhere tightly to the Si substrate not only during the course of cooling from the anode bonding treatment temperature, of about 250° C., to normal (i.e., ambient) temperature but also in the application atmosphere. For this purpose, it is required that (1) the glass substrate should have a thermal expansion coefficient approximately equal to that of Si, (2) the glass substrate should be composed of a glass material having a low softening point, and (3) the glass substrate should have a high resistance to thermal stress. In view of the foregoing, Pyrex glass or lead glass is preferably used. This glass alone can be used as the substrate, or this glass can be used in a state bonded to other glass substrates or an Si substrate.

Under this background, a glass electrode is formed by using the micro-machining technique according to the present invention.

In the glass electrode of the present invention, a thin glass film acting as the sensing film is formed by utilizing at least a part of an $SiO_2$ film obtained by wet oxidation of a wafer.

However, when a glass film having an increased strength is desired, the above-mentioned embodiment of the process for preparing a glass electrode is adopted in the present invention.

The thickness of the $SiO_2$ film formed by the wet oxidation of the silicon wafer is of about 1 $\mu$m in thickness, at the greatest, and it is impossible to increase the film thickness. Accordingly, in the process of the above-mentioned embodiment, a glass substrate is etched in advance to form a glass film having a desired thickness, a silicon oxide film remaining on the surface of the silicon substrate is removed, and then, the glass film is bonded to the bottom portion of the holding hole (i.e., cavity or reservoir).

In the so-prepared glass electrode of the second embodiment of the present invention, the strength of the glass film acting as the sensing film is increased. Therefore, the yield is improved and the glass electrode can be used without breaking.

In the respective glass electrodes obtained according to the above-mentioned two embodiments of the present invention, the sensitivity to the $H^+$ concentration is in practice sufficiently high. However, when a glass electrode having a further enhanced sensitivity is desired, a glass electrode having a structure described below can be adopted.

The voltage generated at the glass electrode is generally represented by the following Nernst equation:

$$E = constant - 0.059 pH \tag{1}$$

However, this equation is a theoretical formula, and it is not easy to construct the glass electrode so that the potential in accordance with this equation is obtained.

When a sensing film is formed by using a Pyrex glass having a thickness of about 50 $\mu$m, the gradient coefficient −0.059 (−59 mV) of the Nernst equation is about −0.03 (−30 mV).

Therefore, the present invention improves the glass material.

Lithium (Li) glass, sodium-calcium (Na-Ca) glass and the like are known as suitable glass materials for a glass electrode. However, in view of the heat resistance and strength limitations thereof, these materials cannot be used as the sensing film for a small glass electrode. The reasons are as follows.

(1) A heat treatment at about 800° C. is necessary for bonding to the Si substrate, for which the heat resistance is insufficient.

(2) A considerable strain is left after heat bonding, which these glass materials cannot resist.

According to the present invention, a double-layer film, used as the sensing film, is obtained by forming a film of a glass material having excellent characteristics, such as a lithium glass or a sodium-calcium glass, by sputtering or vacuum deposition thereof on a film of a glass material which is insufficient as to the characteristics required for the sensing film, such as a Pyrex glass, whereby a glass electrode satisfying, substantially, the requirement of the Nernst equation can be obtained.

In the present invention, it is sufficient if at least one holding hole is formed. However, if a plurality of holding holes are formed and glass films are bonded thereto, the risk of breaking the glass film is effectively reduced.

In the process of the present invention, bonding of the glass substrate and the silicon substrate is accomplished, for example, by a method of heating and bonding both substrates, a method using an adhesive or an anodic bonding method. From a practical viewpoint, the anode bonding method is preferably adopted.

The present invention will now be described in detail with reference to the following examples that by no means limit the scope of the invention.

EXAMPLE 1

FIG. 2(A) is a planar view of a glass substrate 10 of the glass electrode according to one embodiment of the present invention, FIG. 2(B) is a planar view of an Si substrate 20 of the glass electrode according to this embodiment, and FIG. 2(C) is a planar view of the glass electrode of this embodiment of the present invention, formed by inverting and assembling the glass substrate onto the Si substrate 20 and bonding them.

A reference electrode 12 composed of Ag/AgCl, a lead-in line 14 composed of Au and a pad 16 composed of Au are embedded in the glass substrate 10.

The substrate face of the Si substrate 20 is the (100) plane, and the Si substrate 20 is subjected to anisotropic etching, whereby a groove 22 for injecting an electrolyte, an electrolyte-holding hole (i.e., a cavity, or recess) 24 and a glass film 26 acting as the sensing film on at least a part of the hole 24 are formed. Incidentally, the groove only can also be made by the separate anisotropic etching.

In FIG. 2(C), the broken line indicates an interior glass electrode-forming region, and the pad 16 and glass film 26 appear on the side of the Si substrate 20.

Figure 3A:
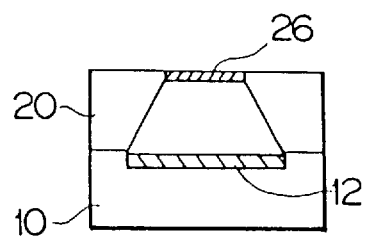
FIG. 3(A) is a cross-sectional view taken along line X—X' in FIG. 2(C) and FIG. 3(B) is a corresponding cross-sectional view showing a modification of the glass electrode according to one embodiment of the present invention.

FIG. 3(A) is a view showing the section taken along X—X' in FIG. 2(C). As is seen from FIG. 2(C) and FIG. 3(A), the sensing film 26 is formed adjacent the bottom portion of the cavity, or reservoir, 26 of the etched Si substrate 20.

Figure 3B:
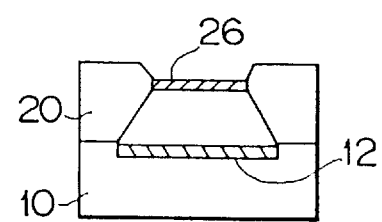

FIG. 3(B) is a sectional view showing a modification of this Example 1, where the Si substrate is etched also from the bottom so that the sensing film 26 is formed slightly on the inner side (i.e., on a recessed interior surface) of the Si substrate.

FIG. 4 is a diagram illustrating the steps of preparing the glass electrode of the present invention. One embodiment of the preparation process will now be described with reference to FIGS. 2(A)–2(C) and FIGS. 4(A)–4(F).

Formation of Glass Substrate:

A negative photoresist is spin-coated on the surface of a Pyrex glass substrate (Iwaki 7740) having a diameter of 2 inches and a thickness of 500 $\mu$m and is heated and dried at 150° C. for 30 minutes. Regions for formation of many reference electrodes 12, lead-in lines 14 and pads 16 are defined by corresponding windows in the photoresist and exposed by photolithography, and the same resist is similarly coated and dried on the back surface.

Then, the glass substrate is immersed in a mixed solution comprising 50% hydrofluoric acid (HF), concentrated nitric acid ($HNO_3$) and ammonium fluoride [$(NH_4)F$] at a ratio of 1/1/8 for 80 minutes to etch the glass substrate to a depth of 3 $\mu$m. Then, the resist is peeled off, by using a mixed solution comprising sulfuric acid ($H_2SO_4$) and hydrogen peroxide ($H_2O_2$) at a ratio of 2/1 [see FIG. 4(A)].

Then, the glass substrate 10 is sufficiently washed with a mixed solution of $H_2O_2$ and ammonia ($NH_4OH$) and pure water, and is then dried.

Then, an Au film is vacuum-deposited on the glass substrate 10. Since Au adheres very poorly to glass, a very thin chromium (Cr) film is vacuum-deposited on the glass substrate in advance to improve the adhesiveness.

The thickness of the Cr film is 400 Å and the thickness of the Au film is 4000 Å.

Then, a positive resist film (DFRP-5000 supplied by Tokyo Oka) is spin-coated, and the resist is coated on regions for forming reference electrodes 12, lead-in lines 14 and pads 16 by the photolithography. Then, the Au film and Cr film are selectively etched to form a reference electrode pattern comprising reference electrodes 12, lead-in lines 14 and pads 16.

The Au-etching solution is formed by dissolving 4 g of KI and 1 g of $I_2$ in 40 ml of water, and the Cr-etching solution is formed by dissolving 0.5 g of NaOH and 1 g of $K_3Fe(CN)_6$ in 4 ml of water.

Then, silver (Ag) is vacuum-deposited on the portion for forming the reference electrode 12, and in the same manner as described above, coating of a positive resist, heat-drying, light exposure and development are carried out to coat the resist only on the reference electrode-forming portion. Then, Ag etching is conducted and the resist is dissolved and removed, whereby a silver film is formed on the reference electrode-forming portion.

The Ag-etching solution is one comprising 29% $NH_4OH$, 31% $H_2O_2$ and pure water at a ratio of 1/1/20.

Then, the entire substrate is sufficiently washed with pure water and immersed in a 0.1 M solution of $FeCl_3$ for 10 minutes to form a thin AgCl layer on the surface of Ag.

Then, the entire substrate is sufficiently washed with pure water to complete reference electrodes 12, lead-in lines 14 and pads 16 [FIG. 4(B)].

Formation of Si Substrate:

An Si substrate 20 having a (100) plane as the substrate face and having a thickness of 350 $\mu$m and a diameter of 2 inches is prepared, sufficiently washed with a mixed solution of $H_2O_2$ and $NH_4OH$ and pure water, and dried. The Si substrate 20 is subjected to wet oxidation at 1050° C. for 200 minutes to form an $SiO_2$ film 28 having a thickness of 1 $\mu$m on the entire surface.

A negative resist (OMR-83 supplied by Tokyo Oka) having a viscosity of 60 cP is coated on the surface of the Si substrate, and light exposure, development and rinsing are carried out to form a resist pattern on the substrate. Then, the Si substrate 20 is immersed in a mixed solution comprising 50% HF and 40% $NH_4F$ at a ratio of 1/6 and the exposed portion of $SiO_2$ is etched and removed to define the surface location of a holding hole (i.e., recess or cavity) 24 to be formed [see FIG. 4(C)].

Then, the resist film is peeled off in a mixed solution comprising sulfuric acid and hydrogen peroxide at a ratio of 2/1. Then, the Si substrate 20 is immersed in 35% KOH at 80° C. and anisotropic etching of silicon is carried out to form the electrolyte-holding hole 24 in the reference electrode portion [see FIG. 4(D)].

A glass film 26 acting as the sensing film is formed adjacent the bottom portion of the holding hole (reservoir) 24 by utilizing an $SiO_2$ film 28 having a thickness of 1 $\mu$m, formed by wet oxidation.

If the $SiO_2$ used as the mask is left on the surface of the Si substrate 20, a higher temperature is necessary for the anodic bonding. Therefore, $SiO_2$ other than the glass film 26 is completely removed by the photolithograhy using a mixed solution comprising 50% HF and 40% $NH_4F$ at a ratio of 1/6. Thus, a vessel portion for storing an electrolyte is completed [see FIG. 4(D)].

Bonding of Glass Substrate and Si Substrate:

The so-prepared glass substrate 10 and Si substrate 20 are immersed in pure water, sufficiently washed under ultrasonic vibrations and dried, and the substrates are bonded to each other by applying a voltage of 1200 V at a temperature of 250° C. across the substrates, with the Si substrate 20 located on the positive side and the glass substrate 10 located on the negative side, whereby the anodic bonding of the glass substrate and the silicon substrate is effected [see FIG. 4(E)].

Many glass electrode elements formed on the substrate are cut out into chips by using a dicing saw to obtain a small glass electrode.

When the so-obtained small glass electrode is used, an electrolyte is introduced into the interior of the electrode according to the following method.

A beaker is charged with 0.1 M hydrochloric acid aqueous solution or an aqueous potassium chloride buffer solution containing a phosphoric acid (electrolyte), and the glass electrode is entirely immersed in the electrolyte and the entire system including the beaker is placed in a sealed vessel. Then, deaeration is carried out by a vacuum pump.

After bubbles have not come out of the groove 22 for injecting the electrolyte 30, air is introduced into the vessel. The hole can be filled with an epoxy resin.

By the above operation, the electrolyte is introduced into the inner space of the electrode, whereby a small glass electrode is obtained [see FIG. 4(F)].

According to this embodiment, a fine glass electrode can be prepared by using the micro-machining technique while maintaining a wafer-like shape.

Accordingly, reduction of the device cost is possible.

Furthermore, since the glass electrode can be stored in a dry state, long-period storage is possible.

EXAMPLE 2

Another embodiment of the process for preparing the glass electrode of the present invention will now be described.

Figures 5A, 5B, 5C:
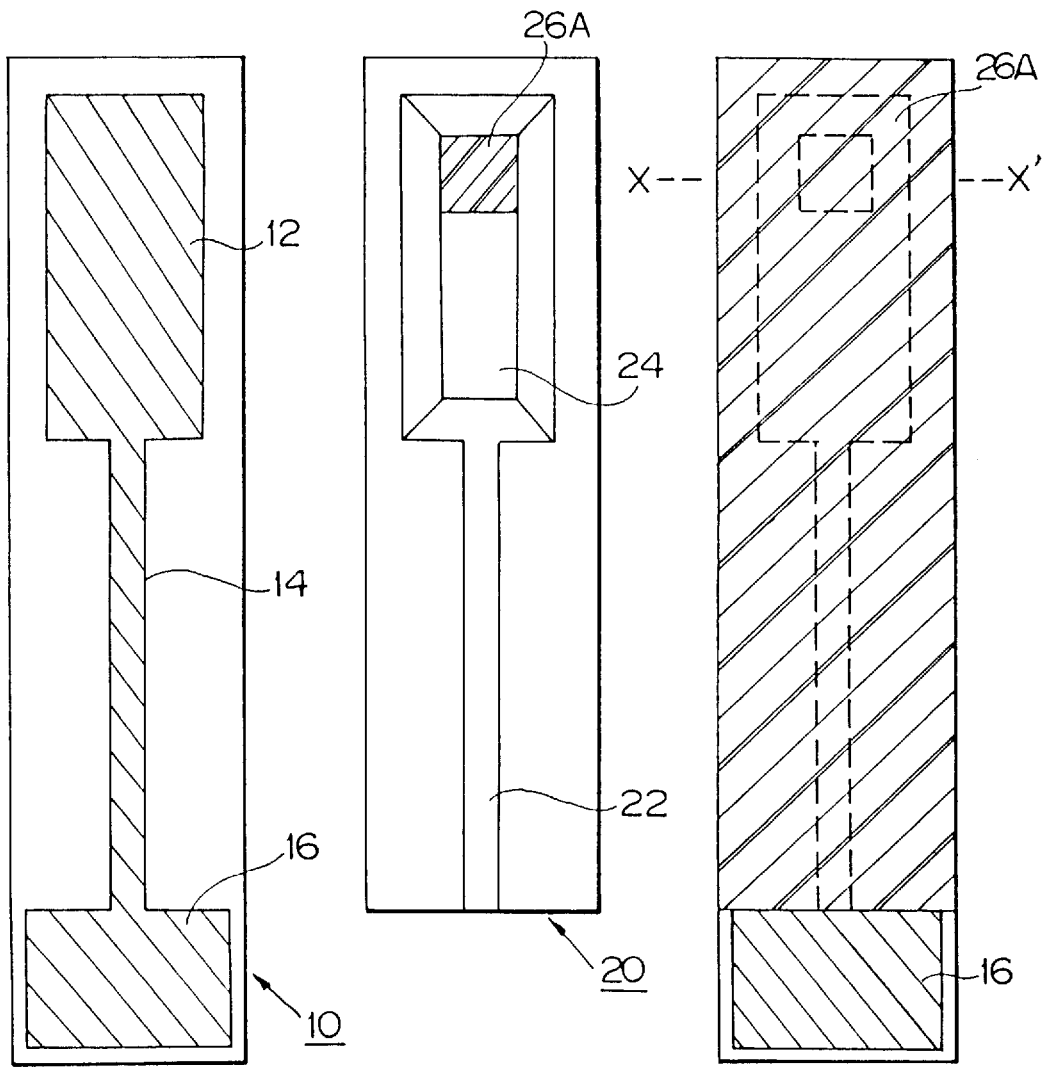
FIG. 5(A) is a planar view of a glass substrate of the glass electrode according to another embodiment of the present invention.
FIG. 5(B) is a planar view of an Si substrate in the glass electrode according to this embodiment.
FIG. 5(C) is a planar view of the glass electrode of this embodiment of the present invention, formed by bonding the glass substrate and Si substrate shown respectively in FIGS. 5(A) and 5(B)

FIG. 5(A) is a planar view of a glass substrate of the glass electrode according to another embodiment of the present invention, FIG. 5(B) is a planar view of an Si substrate of the glass electrode according to this embodiment, and FIG. 5(C) is a planar view of the glass electrode of this embodiment of the present invention, formed by bonding the glass substrate and Si substrate shown respectively in FIGS. 5(A) and 5(B).

Figure 6:
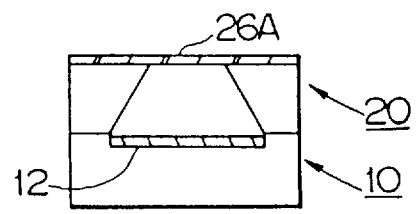
FIG. 6 is a cross-sectional view taken along line X—X' in FIG. 5(C)

FIG. 6 is a cross-section taken along line X—X' in FIG. 5(C).

FIGS. 7(A) to 7(F) are diagrams illustrating steps of forming the glass electrode according to another embodiment of the present invention.

In FIGS. 5(A) through 7(F), the identical reference numerals represent the same members as in FIGS. 1 through 4 unless otherwise indicated.

The glass substrate-forming step is the same as described in Example 1. Accordingly, the description is omitted.

Furthermore, the Si substrate is prepared substantially in the same manner as described in Example 1, except that a part of the $SiO_2$ film is not utilized as the glass film acting as the sensing film, but the $SiO_2$ film is entirely removed.

Bonding of Glass Film to Si Substrate:

A Pyrex glass (Iwaki 7740) is etched in a mixed solution comprising 50% HF and concentrated $HNO_3$ at a ratio of 2/1 to obtain a film having a thickness of about 50 μm, and the film is sufficiently washed to obtain a glass film 26 acting as the sensing film 26A.

Figure 7A:
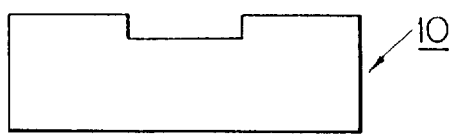
FIGS. 7(A) to 7(F) are diagrams illustrating steps of forming the glass electrode according to another embodiment of the present invention.
Figure 7C:
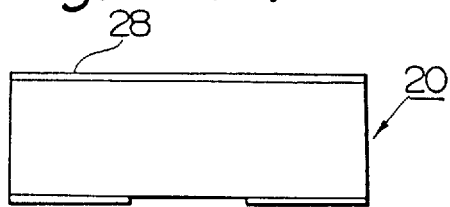
Figure 7B:
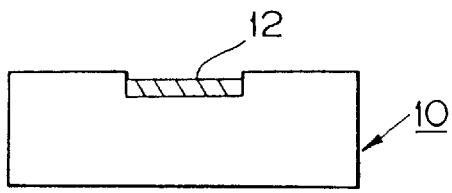
Figure 7D:
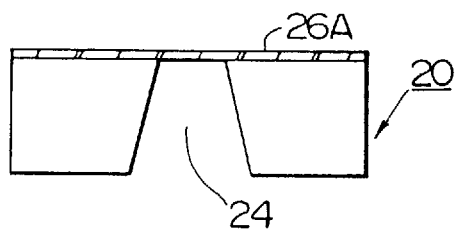

The glass film 26A is placed on the surface of the Si substrate 20, which is previously processed, formed by perforating the Si substrate by the anisotropic etching to include the reservoir 24, and heated at 800° C. to effect bonding [see FIG. 7(D)].

Figure 7E:
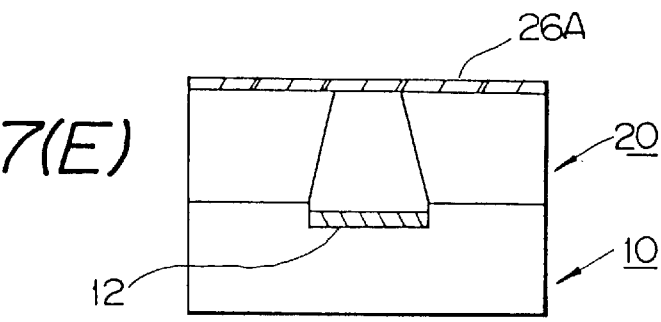
Figure 7F:
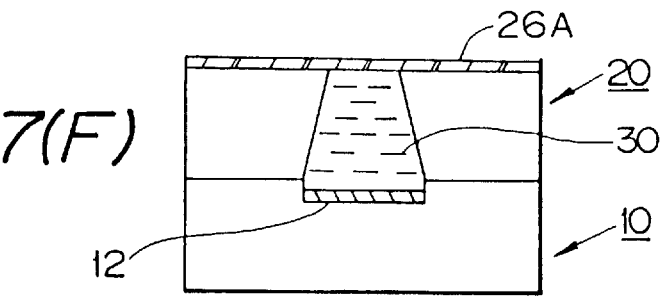

Bonding of the so-prepared glass substrate and Si substrate [FIG. 7(E)] and injection of the electrolyte [FIG. 7(F)] are carried out in the same manner as described in Example 1.

According to this embodiment of the present invention, the strength of the glass film of the formed glass electrode is increased and hence, the yield is increased, and the glass electrode is advantageous over the conventional glass electrode in that no breaking is caused during use.

EXAMPLE 3

Still another embodiment of the process for preparing the glass electrode of the present invention will now be described.

Figures 8A, 8B, 8C:
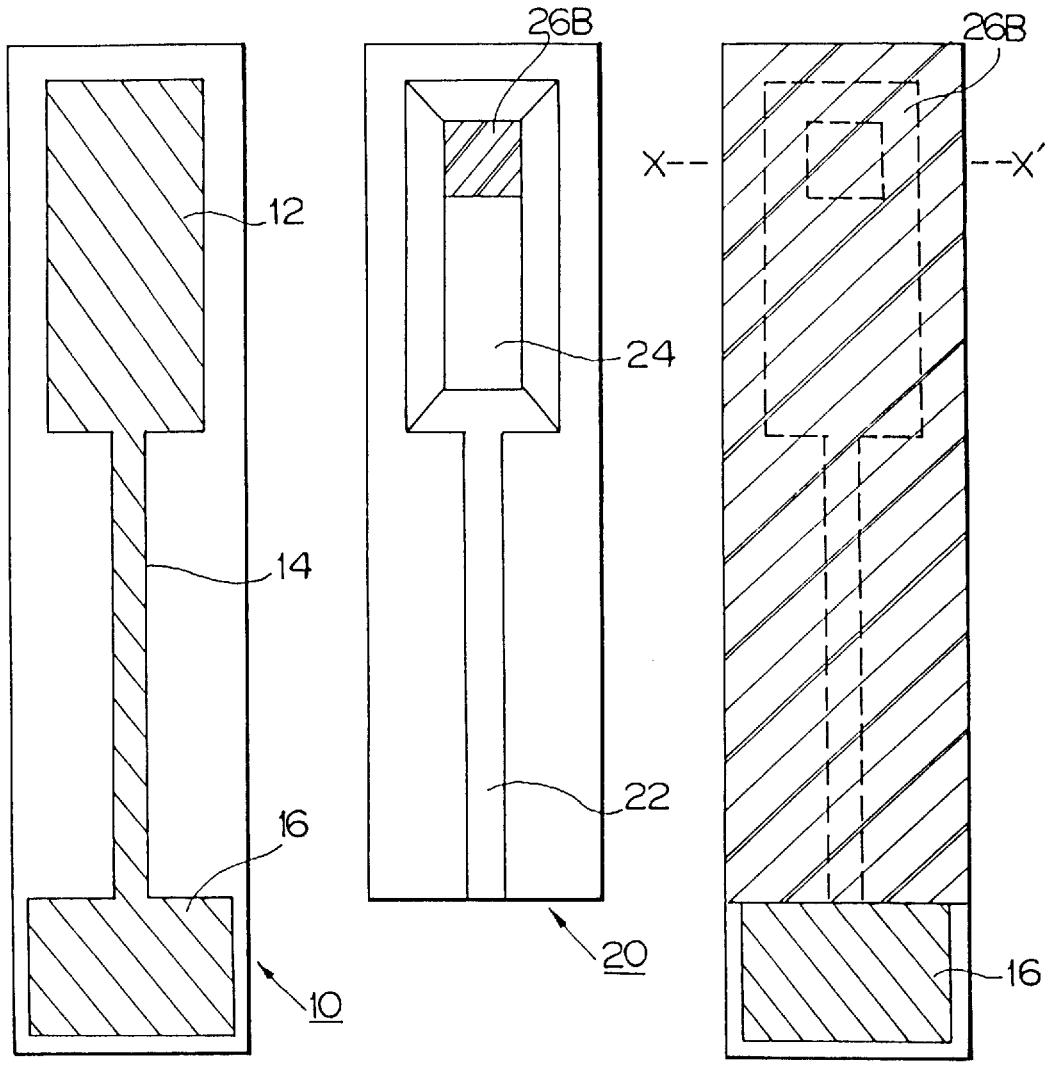
FIG. 8(A) is a planar view of a glass substrate of the glass electrode according to still another embodiment of the present invention.
FIG. 8(B) is a planar view of an Si substrate of the glass electrode according to this embodiment.
FIG. 8(C) is a planar view of the glass electrode of this embodiment of the present invention, formed by bonding the glass substrate and Si substrate shown respectively in FIGS. 8(A) and 8(B)

FIG. 8(A) is a planar view of a glass substrate of the glass electrode according to still another embodiment of the present invention, FIG. 8(B) is a planar view of an Si substrate of the glass electrode according to this embodiment, and FIG. 8(C) is a planar view of the assembled glass electrode of this embodiment of the present invention, formed by bonding the glass substrate and Si substrate respectively shown in FIGS. 8(A) and B(B).

Figure 9:
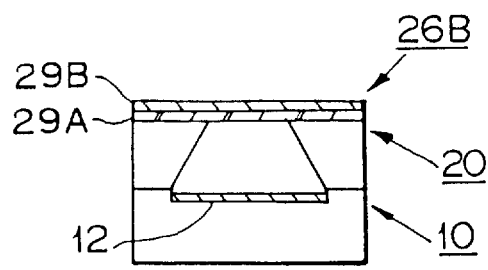
FIG. 9 is a cross-sectional view taken along line X—X' in FIG. 8(C)

FIG. 9 is a cross-section taken along line X—X' in FIG. 8(C).

FIGS. 10(A) to 10(F) are diagrams illustrating steps of forming the glass electrode according to this embodiment of the present invention.

In FIGS. 8(A) through 10(F), identical reference numerals represent the same members as in FIGS. 1 through 4(F) unless otherwise indicated.

The glass substrate-forming step is the same as described in Example 1. Accordingly, the description is omitted.

Furthermore, the Si substrate is prepared substantially in the same manner as described in Example 1, except that a part of the $SiO_2$ film is not utilized as the glass film acting as the sensing film, but the $SiO_2$ film is entirely removed.

Bonding of Glass Film to Si substrate:

A Pyrex glass (Iwaki 7740) is etched in a mixed solution comprising 50% HF and concentrated $HNO_3$ at a ratio of 2/1 to obtain a film having a thickness of, for example, 20–150 μm, in this case 50 μm, and the film is sufficiently washed to obtain a first glass film 29A constituting a film 29A acting as the sensing film.

The first glass film 29A is placed on the back surface of an Si substrate 20 having a perforated or piercing holding hole (reservoir) 24 formed by anisotropic etching of an Si substrate and heated at 750° C. to effect bonding of the first glass film 29A to the Si substrate 20. Then, the Si substrate having the first glass film formed thereon is placed in a sputtering device and an sodium-calcium Na-Ca glass is sputtered in a thickness of 500 nm to form a second glass film 29B on the first glass film 29A, whereby a glass film 26B acting as the sensing film is obtained [see FIG. 10(D)].

Bonding of the so-prepared glass substrate and Si substrate [FIG. 10(E)] and injection of an electrolyte [FIG. 10(F)] are carried out in the same manner as described in Example 1, whereby a small glass electrode is obtained.

The characteristics of the small glass electrode obtained in Example 3 are evaluated according to the following method.

The evaluation is performed by monitoring changes of the potential of the glass electrode relative to the potential of an external reference electrode of silver/silver chloride by using an electrometer. For examining changes of the potential relative to changes of the pH value, the sensing portion of the electrode is immersed in a 10 mM TRIS (Trimethyl aminomethane) solution, and HCl is added to reduce the pH value. At each pH value, the potential of the glass electrode is examined. The experiment is conducted at 25° C.

Figure 11:
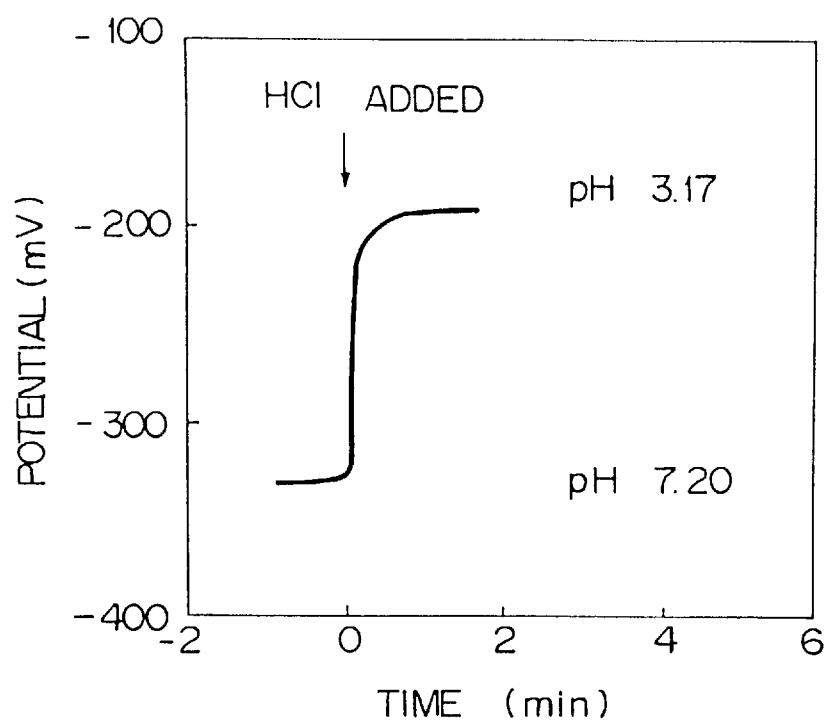
FIG. 11 is a diagram illustrating a response curve of the glass electrode of the present invention.

The response curve obtained when the pH value of the external buffer solution is changed is shown in FIG. 11.

Figure 12:
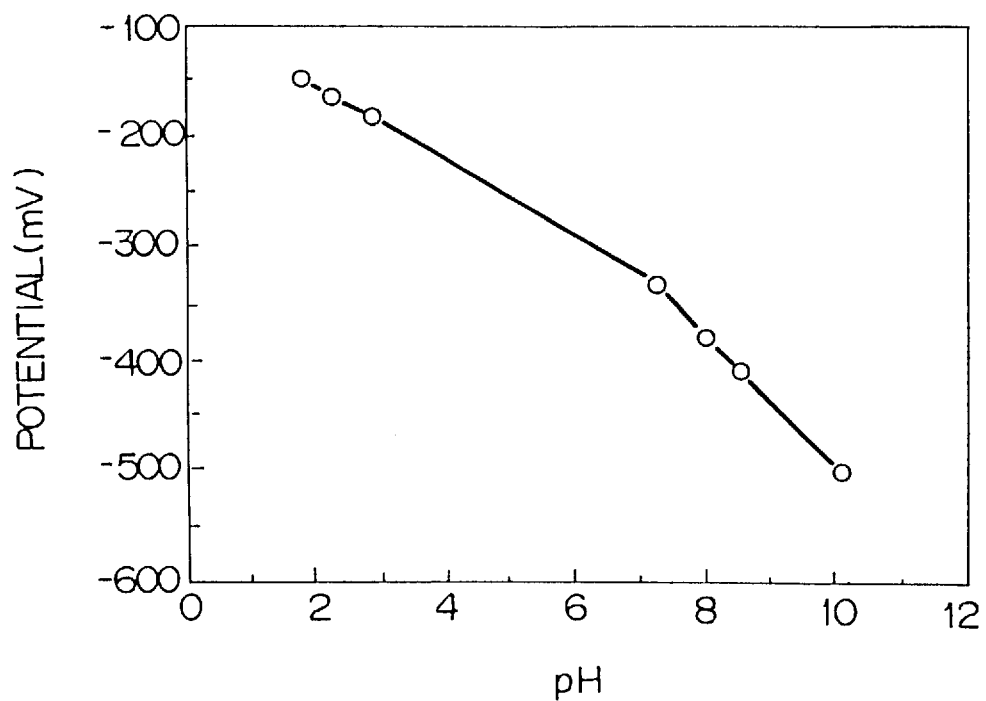
FIG. 12 is a curve illustrating the relation between the change of the $H^+$ concentration and the change of the electrode potential in the glass electrode of the present invention.

As is seen from FIG. 11, a very clear response curve is obtained. When the pH value is changed, the small glass electrode immediately shows a change and a 90% response time is 10 seconds. A change of the electrode potential observed when the pH value is changed is shown in FIG. 12. It is seen that a linear relation is established between them over a broad pH value range of from 2 to 10. The gradient of the linear relation is a value approximate to −59 mV/pH of the theoretical value of the Nernst equation at 25° C.

As before noted, the second embodiment of the invention provides a small glass electrode which includes reference electrodes. As a result, a separate reference electrode is not necessary and therefore this small glass electrode is convenient in practical use.

The insulating substrate, i.e., the substrate for the electrode body, of this embodiment may be a semiconductor substrate, particularly a silicon substrate, or a glass substrate, a ceramic substrate, etc. When a silicon substrate is used, it should be insulated and the insulating layer over the silicon substrate can be a silicon oxide layer or other insulating layer. The silicon oxide layer can be easily formed by thermal oxidation of a silicon substrate. A silicon nitride layer is not appropriate since it does not allow anodic bonding to be used. A most preferred substrate is 7740 glass (so-called Pyrex glass) or various glass substrate with a thin 7740 glass layer attached thereto.

The silicon substrate in which a recess for storing an electrolyte is to be formed is preferably a silicon substrate having a top surface of (100) plane which is suitable for an anisotropic etching.

The reference electrode for detecting a change of the potential of the glass film can be selected from a wide range, but a silver/silver chloride electrode is suitable for the thin film process.

The electrodes may be preferably formed by deposition processes such as evaporation or sputtering.

The electrolyte is selected 33A so that the reference electrode can work normally. For example, if a silver/silver chloride electrode is used, an aqueous solution of potassium chloride or the like which contains a chloride ion is used.

EXAMPLE

A preferred example of a small glass complex electrode in accordance with the second embodiment of the present invention and a process of manufacturing the same are described below.

FIGS. 13A and 13B are front and rear surfaces of a preferred small glass complex electrode and FIG. 13C in a cross-sectional view of the small glass complex electrode. This small glass electrode is made by bonding a glass substrate 31 and two silicon substrates 32A and 32B. This glass electrode has a rectangular shape.

Portions 38A and 38B of reference electrodes 33A and 33B are exposed. The reference electrodes of the example are silver/silver chloride electrodes, formed on gold electrodes.

Figure 14A:
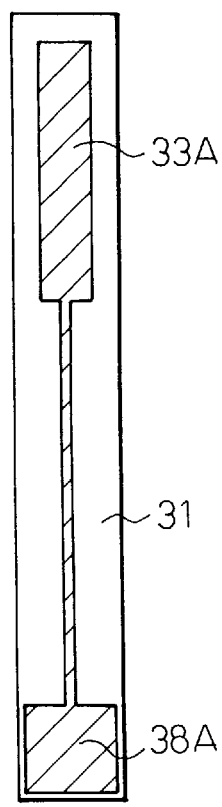
FIGS. 14A and 14B are plan views of an inside reference electrode portion and an inside reference electrode container portion of the device of the second embodiment.
Figure 14B:
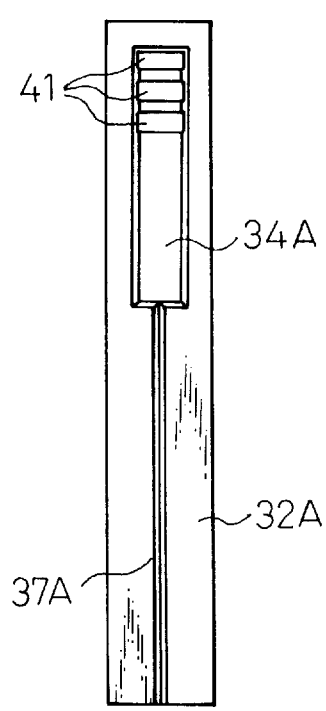
Figure 15A:
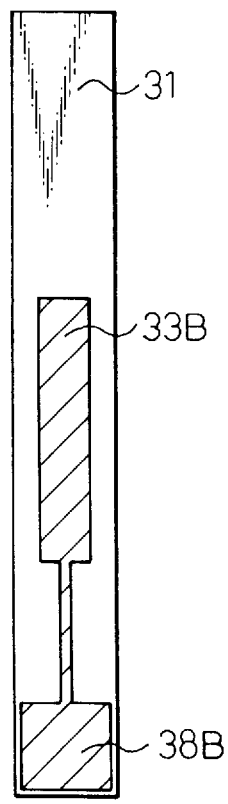
FIGS. 15A and 15B are plan views of an outer reference electrode portion and an outside reference electrode portion of the device of the second embodiment.
Figure 15B:
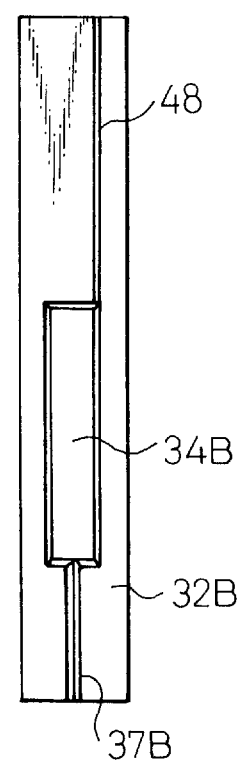

The structure of a small glass complex electrode shown in FIGS. 13A to 13C can be understood from plan views of an electrode substrate 31 on the side of an inside reference electrode 33A and a container substrate 32A, before they are bonded, as shown in FIGS. 14A and 14B, and from plan views of the electrode substrate 31 on the side of an outside reference electrode 33B and a container substrate 32B, before they are bonded, as shown in FIGS. 15A and 15B. The glass substrate 31 has the inside reference electrode 33A as shown in FIG. 14A and the outside reference electrode 33B as shown in FIG. 15A. The silicon substrate 32A has a dent portion 34A formed at a location corresponding to the inside reference electrode 33A by anisotropic etching and for storing an electrolyte, as shown in FIG. 14B. A thin glass film 35 is adhered over the dent portion 34A to the silicon substrate 32A, as shown in FIG. 13C. The silicon substrate 32B has a dent portion 34B formed at a location corresponding to the outside reference electrode 33B and for storing an electrolyte, the dent portion 34B being able to be electrically connected to the outside of the electrode through a salt bridge 48, as shown in FIG. 15B. The dent portions 34A and 34B of the silicon substrates 32A and 32B are filled with an electrolyte 36 of saturated aqueous potassium chloride solution having a predetermined pH, after the electrode is manufactured. The silicon substrates 32A and 32B have grooves 37A and 37B near pads 38A and 38B for pouring the electrolyte into the small dent or recess portions 34A to 34B.

The small glass electrode as shown in FIGS. 13A to 13C can be advantageously manufactured by a process shown in FIGS. 16A to 16K. It should be noted that a plurality of small glass electrodes are simultaneously manufactured in a single wafer, while only one small glass electrode is described and illustrated below. In FIGS. 16A to 16K, only a sensing portion of a small glass electrode is illustrated in sectional views.

(1) Manufacture of Electrode Substrate a) Chromium was deposited on both surfaces of a disc of 7740 glass (so-called Pyrex, made by Iwaki Glass) 31 having a diameter of 3 inches and a thickness of 500 $\mu$m. The chromium layers had a thickness of 40 nm. On both surfaces of the substrate 31, negative-type photoresist layers having the same patterns as those of reference electrodes 33A and 33B to be formed later were formed by a double sided exposure unit. Here, the portions where the reference electrodes 33A and 33B were to be formed were exposed. After the resist patterns were made, the resist layers were baked at 150° C. for 30 minutes.

b) The substrate was immersed in chromium etching solution (0.5 g KOH and 1 g $K_3Fe(CN)_6$ in 4 ml water) to remove the exposed portions of the chromium layers.

c) The substrate was immersed in 50% hydrofluoric acid cooled with ice to etch the exposed portions of the glass to a depth of 9 $\mu$m.

d) The photoresist layers formed in the step a) were removed in a mixed sulfuric acid and hydrogen peroxide solution (mixing ratio of 2:1). Thus, grooves 33A' and 33B' having a depth larger than the thickness of the reference electrodes 33A and 33B to be formed were made. (FIG. 16A).

e) The substrate was cleaned with a mixed hydrogen peroxide and ammonia solution and with pure water, and then dried.

f) A gold layer was deposited in a vacuum onto both surfaces of the substrate. A chromium layer was inserted between the substrate and the gold layer to improve the poor adhesion of the gold layer to the substrate. The thickness of the chromium and gold layers were 40 nm and 400 nm, respectively.

g) A positive type photoresist layer (OFPR-5000, made by Tokyo Ohka) was formed on both surfaces of the substrate.

h) The photoresist layers were patterned to the same patterns as used in the step a), to obtain resist patterns covering reference electrodes 33A and 33B, lead lines and pad portions 38A and 38B.

i) The substrate with the resist patterns was immersed in a gold etching solution (4 g KI and 1 g $I_2$ in 40 ml water) to remove the exposed portions of the gold. The substrate was cleaned with pure water. The resist layers were than removed with acetone.

j) The substrate was immersed in an etching solution as used in the step b) to remove the exposed portions of the chromium layer.

k) The substrate was cleaned with pure water and dried.

l) Silver was then deposited on both surfaces of the substrate to a thickness of 400 nm. In the step k), it is preferred that the gold electrode patterns also cover the reference electrodes in order to improve the adhesion.

m) Positive-type photoresist layers were coated on both surfaces of the substrate, baked, exposed and developed to form photoresist patterns only on the portions where the reference electrodes were to be formed.

n) The substrate with the resist layers was immersed in a mixed solution of 29% ammonia, 31% hydrogen peroxide and pure water at a ratio of 1:1:20 to etch the silver.

o) The substrate was cleaned with pure water.

The electrode body was obtained after the above operations a) to o) (FIG. 16B).

(2) Manufacture of Container Portions a) Silicon wafers 32A and 32B having a diameter of 3 inches, a thickness of 200 $\mu$m and a top surface of (100) plane were prepared and cleaned with a mixed hydrogen peroxide and ammonia solution and with a conc. nitric acid and then rinsed with pure water.

b) The silicon wafer was thermally oxidized in wet conditions at 1050° C. for 200 minutes to form $SiO_2$ layers 39 over all the surfaces of the wafer.

c) Negative photoresist layers (OMR-83, made by Tokyo Ohka; viscosity of 100 cP) were coated on the silicon substrates 32A and 32B, exposed, developed and rinsed, to form resist patterns for etching on the wafers. In this example, since the silicon substrate 32A has a penetrated hole, it is advantageous that the silicon substrate 32A is etched from both surfaces. Therefore, in this case, the resist patterns were formed on both surfaces of the silicon substrate 32A.

d) The wafers were immersed in a 50% hydrofluoric acid and 40% ammonium fluoride solution (a mixing ratio of 1:6) to remove the exposed portions of the $SiO_2$ layers 39 (FIGS. 16C and 16D).

e) The negative-type photoresist layers were removed in a mixed solution of sulfuric acid and hydrogen peroxide at a mixing ratio of 2:1.

f) The silicon substrates 32A and 32B were immersed in 35%-KOH to perform anisotropic etching of the silicon substrates 32A and 32B. After this etching, containers having cavities 34A and 34B for storing an electrolyte in the reference electrode portions were obtained. At the sensing portion 35 of the silicon substrate 32A for the inside reference electrode, the etching was conducted until a hole 34A was opened.

g) If the $SiO_2$ layers remain on the surfaces of the silicon substrates, the anodic bonding at the later step (3) requires a higher temperature. Accordingly, the $SiO_2$ layers were completely removed by the same etching solution as used in the step d).

Thus, container portions 32A and 32B were completed after the operations a) to g).

It is noted that two substrates for an inside reference electrode and outside reference electrode are prepared in this embodiment, the steps are the same for both substrates while the patterns are different.

Figure 16G:
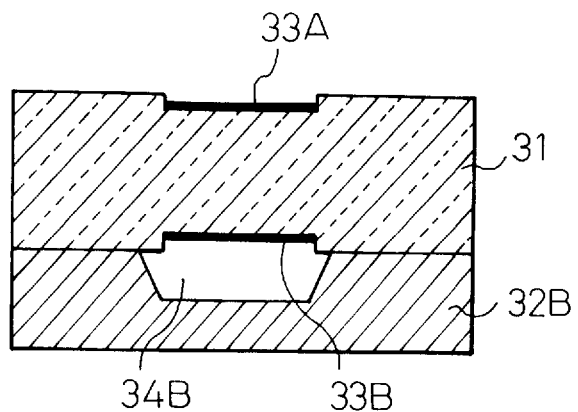
FIGS. 16A to 16M are sectional views of a small glass electrode as shown in FIGS. 13A to 13C and a variation of this small glass electrode in some main steps of manufacturing the same.

(3) Bonding of Electrode Substrate and Container Substrates a) The electrode substrate 31 and the silicon container substrate 32B for the outside reference electrode, obtained by the above steps (1) and (2), were immersed in pure water and cleaned with supersonic waves.

b) The alignment of the pattern 33B of the glass substrate 31 with the dent portion 34B of the silicon substrate 32B was made in a clean atmosphere.

c) An electric voltage of 1200 V was applied between the glass and silicon substrates 31 and 32B at 250° C. to cause anodic bonding of these substrates. A negative potential was applied to the glass substrate 31. (FIG. 16G)

(4) Formation of Resist Pattern for Bonding

Figure 16H:
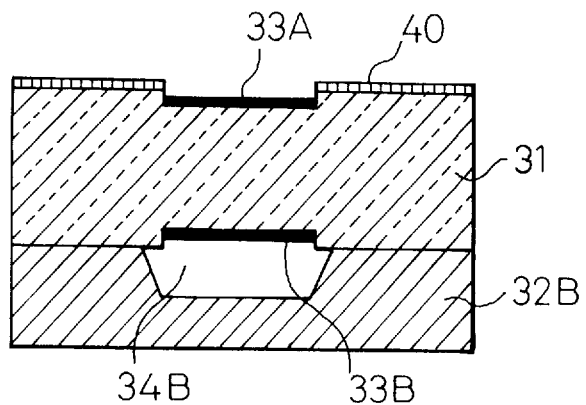

A negative-type photoresist (OMR-83, made by Tokyo Ohka) 40 was coated and patterned on the anodic bonded glass substrate on the side where the inside reference electrode 33A was formed. The resist pattern covered the entire substrate except for the pattern of the reference electrode (including the lead line and pad). (FIG. 16H)

Figure 16I:
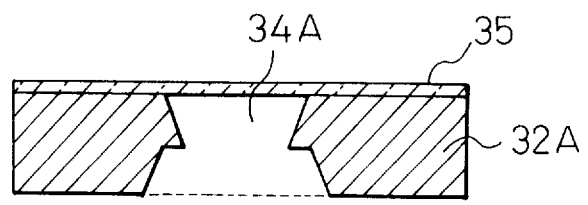
Figure 16:
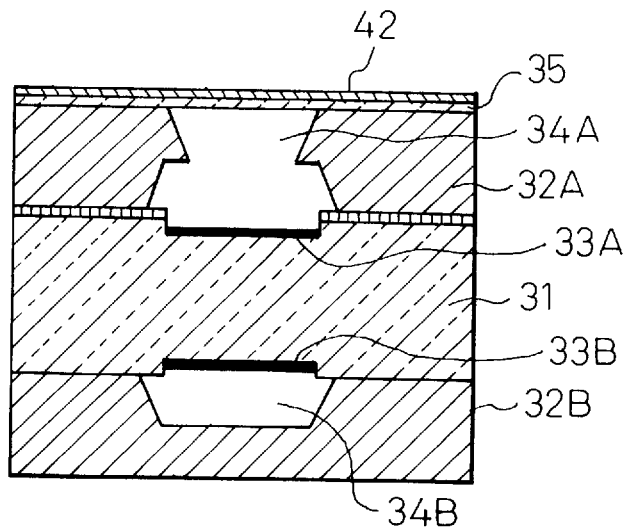
Figure 16:
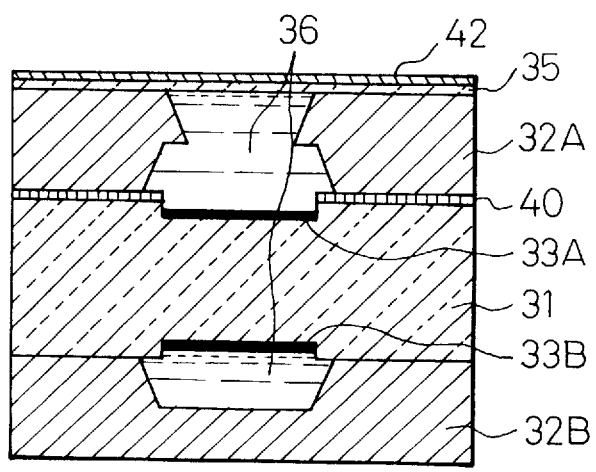

(5) Bonding and Formation of Glass Sensing Film a) A glass substrate of 7740 glass, identical to that used in the step (1), was cleaned and anodic bonded onto the silicon substrate 32A for the inside reference electrode 33A. The conditions of this anodic bonding were the same as those in the above step (3). Thus, a glass plate 35 was bonded over the sensing portion of the silicon substrate 32A.

b) The glass plate 35 was polished by a dicing saw to a thickness of 20 $\mu$m to form a glass film sensing portion. (FIG. 16I)

c) The thus bonded substrates were immersed in pure water and cleaned with supersonic waves, then with a mixed solution of hydrogen peroxide and ammonia. The substrates were then dried by a dry nitrogen gas.

(6) Bonding of Substrate a) The glass substrate 31 was aligned with the silicon substrate 32A.

b) The aligned glass and silicon substrate 31 and 32A were heated to 1500C, by which the substrates were bonded through the negative-type photoresist 40.

(7) Sputtering of Sensing Film

A sodium calcium glass film 42 was sputtered to a thickness of 5 $\mu$m on the glass substrate 35 where it was polished by dicing saw. (FIG. 16J)

(8) Formation of Silver Chloride Layer a) The wafer, as a whole, was immersed in a 100 $\mu$M-aqueous solution of $FeCl_3$ in a beaker and an evacuation was effected to introduce the solution into the cavities 34A and 34B, in order to form a silver chloride layer on the surfaces of the silver layers of the inner and outer reference electrodes.

b) After the immersion was continued for 5 minutes, evacuation or baking of the substrates was conducted to remove water content.

(9) Dicing of Substrates

The substrates were diced by a dicing saw to obtain a large number of glass electrodes in the form of chips.

(10) Insulation of Sides

The sides of the glass electrodes exposed by the dicing were insulated by polystyrene and a negative-type photoresist.

(11) Introduction of Electrolyte

An electrolyte 36 can be easily introduced into the cavities 34A and 34B by the following operations.

a) A saturated KCl aqueous electrolyte solution having a certain pH is charged in a beaker, in which a small glass electrode, as a whole, is immersed. The beaker is set in a closed container and it is evacuated by a vacuum pump.

b) After it is confirmed that no more air bubbles exit from the electrolyte pouring ports 37A, 37B and 48, air is introduced into the container. By these operations, the electrolyte 36 is introduced into the cavities 34A and 34B of the glass electrode.

c) If air bubbles still remain around the sensing portion of the glass electrode, the steps or operations a) and b) must be repeated.

Since the cavity 34B of the outside reference electrode side communicates with the exterior through a salt bridge 48, the electrolyte therein can be easily flown out. To prevent this, it is preferred that the electrolyte is impregnated in a gel. This can be carried out by the following operations.

a') 50 ml of aqueous $CaCl_2$ solution is charged in a beaker, in which a small glass electrode is immersed and an evacuation operation is conducted to introduce the aqueous $CaCl_2$ solution in the cavities.

b') The outside of the glass electrode chip is cleaned and dried in a vacuum to remove water content in the solution, to thereby deposit $CaCl_2$ on the wall surface of the cavities.

c') An aqueous solution of sodium alginate and electrolyte is introduced into the cavities by a similar evacuation process. Then, $CaCl_2$ begins to be dissolved in the solution, to thereby form a calcium alginate gel.

After these steps (1) to (11), a small glass complex electrode which can be actually used is obtained.

The small glass electrode is used by immersing the sensing portion of the electrode in a solution to be measured and determining an electric voltage change between the inner and outer reference electrodes.

Although one glass substrate and two silicon substrates are used in this example, only one silicon substrate may be used, in which case the inside and outside reference electrodes are formed on the same surface of a glass substrate. Use of two silicon substrates is however advantageous since two containers or cavities for the two reference electrodes must be completely electrically insulated and since the glass sensing film would have a width narrower than the width of a glass electrode comprising two silicon substrates.

The glass film portion is not broken during the formation of the glass electrode. Accordingly, this glass electrode can be manufactured at a yield of nearly 100%.

Figure 16L:
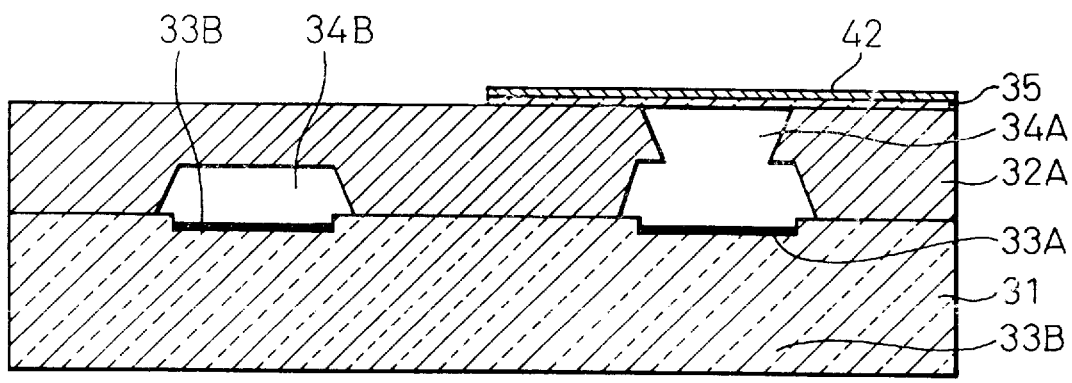
Figure 16M:
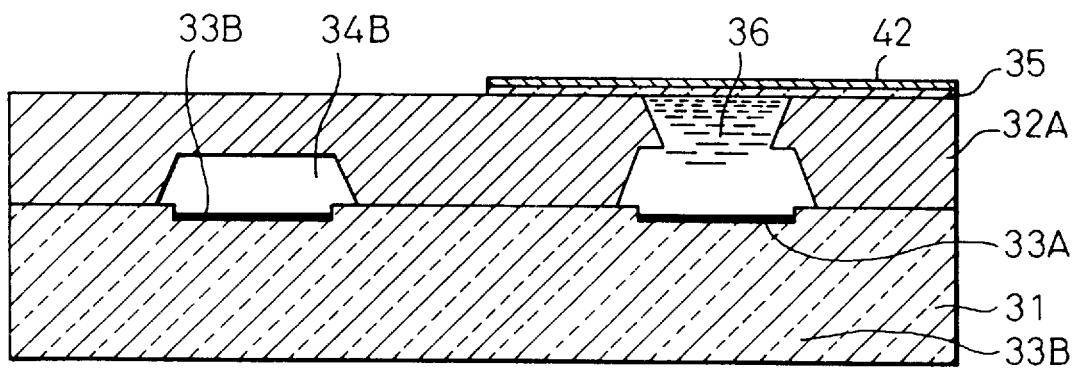

The use of only one silicon substrate, mentioned above, is shown in FIGS. 16L and 16M which correspond respectively to FIGS. 16J and 16K. A planar insulating substrate 31 has inside reference electrode 33a and outside reference electrode 33B formed on a surface of the insulating substrate 31. A silicon substrate 32A is bonded onto the insulating substrate 31, and the silicon substrate 32A has first and second dent portions 34A, 34B which cover the inside and outside reference electrodes 33A, 33B, respectively. The silicon substrate 32A has a penetrating hole formed in a portion of the first dent portion 34A, and the penetrating hole is covered by a glass sensing film 35 bonded onto the silicon substrate 32A. The second dent portion 34B for the outside reference electrode 33B communicates with the exterior through a salt bridge. The first and second dent portions 34A, 34B form storage places. An electrolyte 36 fills the first and second dent portions 34A, 34B which are insulated from each other.

As before noted, the output of a glass electrode may be affected by temperature. It is therefore preferable that a glass electrode is combined with a temperature sensor. For this purpose, a small glass electrode of the third embodiment of the present invention is combined with a temperature sensor as described below.

Figure 17A:
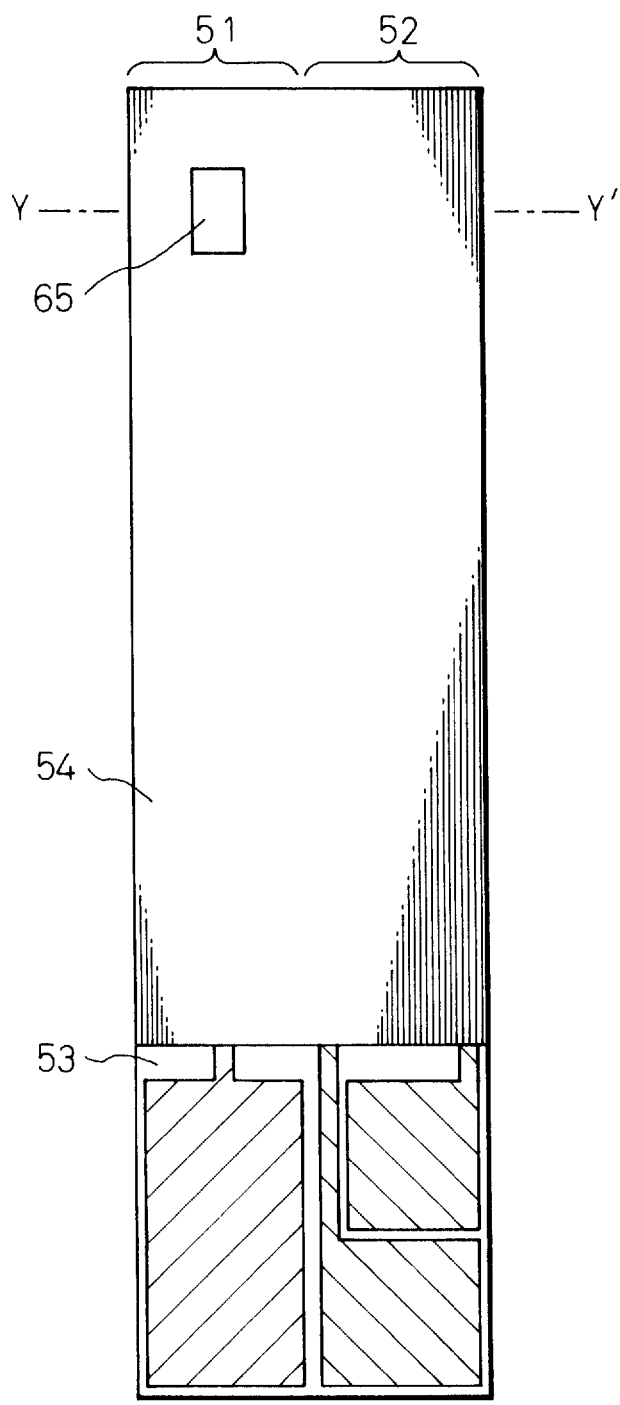
Figure 17B:
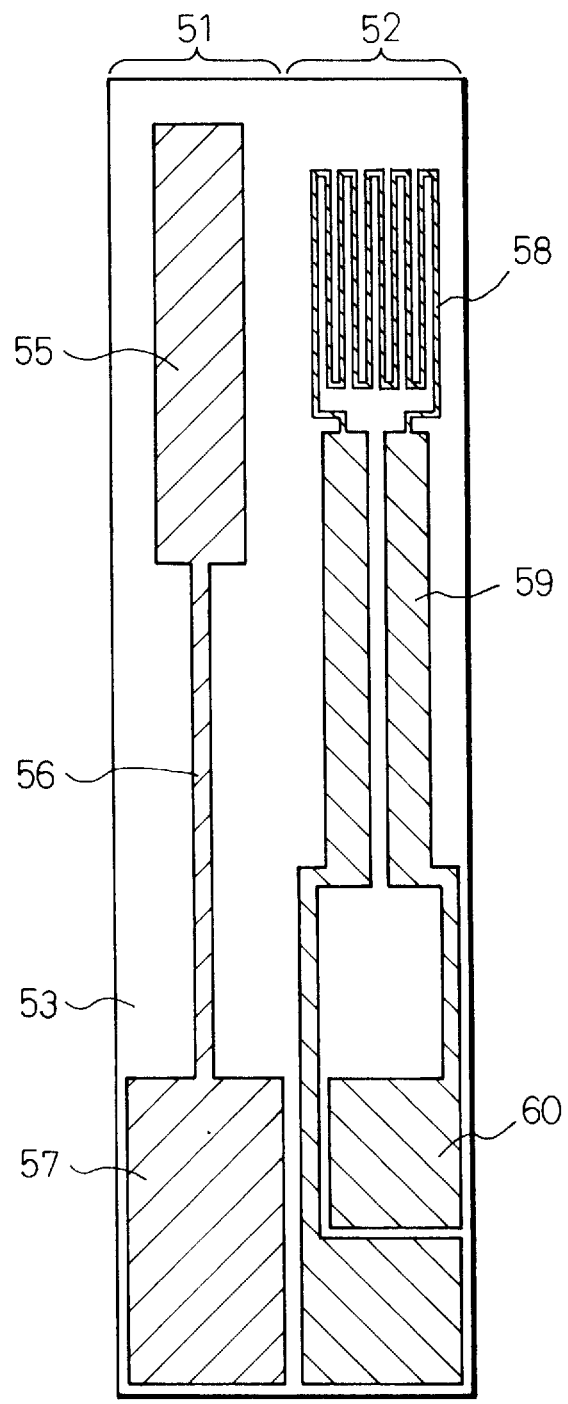

FIGS. 17A to 17C illustrate an example of a small glass electrode combined with a temperature sensor. FIG. 17A is a plan view of such a small glass electrode. FIGS. 17B and 17C are plan views of two substrates to be bonded to each other. The surfaces of the two substrates shown in FIGS. 17B and 17C are those to be bonded.

The small glass electrode includes a portion 51 of a glass electrode and a portion 52 of a temperature sensor.

The small glass electrode comprises a glass substrate 53 and a silicon substrate 54, which are directly bonded to each other by anodic bonding.

On the glass substrate 53, a reference electrode 55, a lead-in line 56, and a pad 57 are formed in the glass electrode portion 51, and a thin film resistor 58 as a temperature sensing element, lead-in lines 59 and pads 60 are formed in the temperature sensor portion 52.

In FIG. 17C, the silicon substrate 54 has a dent or hole 62 for containing an electrolyte and a groove 63 is formed in the glass electrode portion 51. There is a through-hole 64 in the silicon substrate 54 on at least a part of the dent.

Referring to FIG. 17A, a glass film 65 which can act as a sensing film covers the hole 64 on the exterior side of the silicon substrate 54. The glass film 65 must be hydrogen ion selective.

The portion 51 of a glass electrode is the same as described before.

The portion 52 of a temperature sensor comprises a thin film resistor 58 of gold which is sandwiched by the glass substrate 53 and the silicon substrate 54, in order to protect the thin film resistor 58 as a temperature sensing element from the environment. The thin film resistor 58 comprises a long narrow gold pattern so as to constitute a resistor. For example, the gold pattern 58 has a width of 50 $\mu$m, a thickness of 4000 Å and a length of 30 mm, which corresponds to an electrical resistance of 60 $\Omega$.

The lead lines 59 and pads 60 may be formed from the same gold layer. For example, the lead lines 59 has a width of 500 μm and a length of 5 mm, which corresponds to an electrical resistance of 1 Ω. Thus, the electrical resistance of the leads 59 and pads 60 can be neglected in comparison with that of the thin film resistor 58.

The thin film resistor 58 may be made of various pure metals such as platinum, silver or copper or of a thermistor material such as certain semiconductors, if the electrical resistance of the material is changed with the temperature.

It is preferred that the thin film resistor 58 and the leads 59, are completely housed in the bonded substrates 53 and 54, by forming a dent or shallow groove on the surfaces of the glass and/or silicon substrates 53 and 54. In this case, since a groove for housing or seating the reference electrode 55 and the lead line 56 is formed on the surface of the glass substrate 53, the groove for housing or seating the thin film resistor 58 and the leads 59 is preferably formed on the same surface of the glass substrate 53 in the same etching step.

Figure 18A:
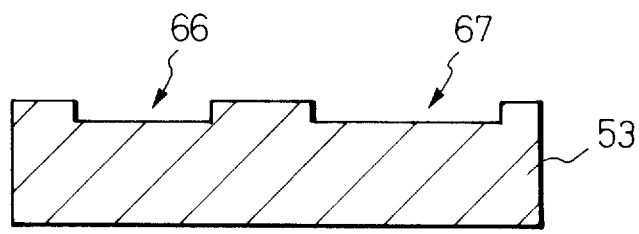
FIGS. 18A to 18C are sectional views of the two substrates and the glass electrode, taken in a plane along the line 18A—18A to 18C—18C, respectively, in FIG. 17A.

FIG. 18A show a cross section of the glass substrate 53 in a plane along the line 18A—18A in FIG. 17A. The glass substrate 53 is coated with a photoresist which is patterned by a photolithographic process. This glass substrate is then etched using the patterned photoresist as a mask, to obtain grooves 66 and 67, in which the reference electrode 55, the thin film resistor 58, the leads 56 and 59 and the pads 57 and 60 are to be seated.

After removing the photoresist from the glass substrate 53, chromium and then gold are deposited. The deposited gold and chromium layers are selectively etched in the manner described before. In this patterning of the gold and chromium layers, a glass electrode pattern of the reference electrode 55, the lead 56 and the pad 57 as well as a temperature sensor pattern of the thin film resistor 58, the leads 59 and the pads 60 are obtained. The chromium layer is inserted in order to improve the adhesion of the gold to the glass substrate. The reference electrode 55 of silver/silver chloride can be formed in the manner as described before.

Figure 18B:
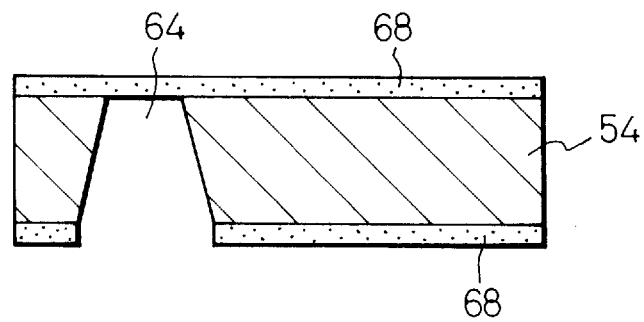

FIG. 18B shows a cross section of the silicon substrate 54 also in a plane along the line 18A—18A in FIG. 17A. The dent or groove 62 and the through hole 64 are formed by anisotropic etching in the manner as described before. By this anisotropic etching, the temperature sensor portion 52 is however not etched. After the anisotropic etching the hole 64 is formed, but the thermally oxidized film (i.e., glass film) 68 remains at the bottom of the hole 64 on the exterior surface side of the silicon substrate 54, which glass film can act as a hydrogen ion selective sensing film. The thermally oxidized film 68 still substantially covering the silicon substrate 54 is etched off except for a portion 65 covering the hole 64, in order to facilitate the anodic bonding of the silicon substrate 54 to the glass substrate 53.

Figure 18C:
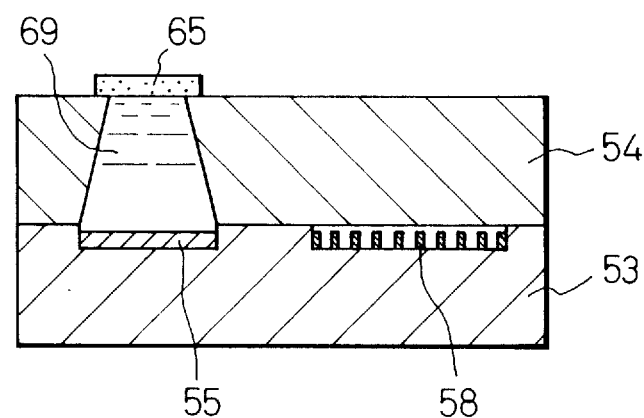

FIG. 18C is a cross section of the complete glass electrode in a plane also along the line 18A—18A in FIG. 17A. The glass substrate 53 and the silicon substrate 54 are directly bonded to each other.

Thus, a small glass electrode provided with a temperature sensor as shown in FIG. 17A is completed. An electrolyte 69 is injected into the dent 62 through the groove 63. It is preferred that the entrance of the groove 67 is sealed, for example, by a suitable resin, before the glass electrode is immersed in an electrolyte solution to inject the electrolyte in the dent 62 of the glass electrode.

It should be understood that a plurality of glass electrodes each provided with a temperature sensor, as described above, can be simultaneously manufactured in a wafer using a microprocessing technique, which allows the production cost to be significantly lowered.

In the above example, a glass substrate is used as a substrate for carrying the reference electrode, etc., and a silicon substrate is used as a substrate for an electrolyte container and a thin film resistor protector. Nevertheless, these substrates are not particularly limited. For example, a silicon substrate may be used as a carrying substrate, by forming a insulating layer at portions of the substrate where the conductor, such as gold/chromium layers, is to be formed. The silicon substrate may be replaced by a glass substrate.

What is claimed is:

1. A small glass electrode having a bonded structure comprising:

a planar glass substrate having a first main surface and having embedded therein, from the first main surface, an inside reference electrode, a first pad and a first lead-in line interconnecting said inside reference electrode and said first pad, said planar glass substrate having a second main surface and having embedded therein, from the second main surface, an outside reference electrode, a second pad and a second lead-in line interconnecting said outside reference electrode and said second pad;

a first silicon semiconductor substrate bonded to the first main surface of said glass substrate and having a first main surface, at least one reservoir extending into the first silicon semiconductor substrate from the first main surface for holding an aqueous electrolyte and a groove forming a fluid passageway in communication with the reservoir for injecting the aqueous electrolyte into the reservoir, said groove and said reservoir being formed by anisotropic etching of the first silicon semiconductor substrate, the reservoir extending from the first main surface and toward a second opposite main surface of the first silicon semiconductor substrate and the reservoir having a sidewall defining an aperture at the second main surface of the first silicon semiconductor substrate to expose the interior of the reservoir, the aperture being disposed at a location corresponding to the position of the inside reference electrode embedded in the glass substrate;

a glass sensing film covering and sealing the aperture in the sidewall and thus at a position corresponding to said inside reference electrode; and a second silicon semiconductor substrate bonded to the second main surface of said glass substrate and having a first main surface, at least one reservoir extending into the second silicon semiconductor substrate from the first main surface for holding an aqueous electrolyte and a groove for forming a salt bridge communicating between the reservoir and the exterior, said groove and reservoir being formed by anisotropic etching of the second silicon semiconductor substrate, the reservoir covering said outside reference electrode.

2. A small glass electrode according to claim 1, wherein an electrolyte occupies the electrolyte-holding reservoirs.

3. A small glass electrode according to claim 1, wherein said inside and outside reference electrodes are composed of silver/silver chloride.

4. A small glass electrode according to claim 1, wherein said first and second pads and lead-in lines are made of gold or platinum.

5. A small glass electrode according to claim 1, further comprising a temperature sensor.

6. A small glass electrode according to claim 5, wherein said temperature sensor comprises a thin film resistor formed between the glass substrate and the first or second silicon semiconductor substrate.

7. A small glass electrode according to claim 1, wherein the glass sensing film comprises two layers of glass film.

8. A small glass electrode according to claim 1, wherein said first and second silicon semiconductor substrates are (100) oriented silicon semiconductor substrates.

9. A small glass electrode having a bonded structure comprising:
- a glass substrate having a main surface and having embedded therein from the main surface, an inside reference electrode, a first pad, a first lead-in line interconnecting said inside reference electrode and said first pad, an outside reference electrode, a second pad, and a second lead-in line interconnecting said outside reference electrode and said second pad, said inside reference electrode, said first pad and said first lead-in line being electrically isolated from said outside reference electrode, said second pad and said second lead-in line;
- a silicon semiconductor substrate having a first main surface, at least one first reservoir extending into the silicon semiconductor substrate from the first main surface for holding an aqueous electrolyte, a first groove forming a passageway in communication with the first reservoir for injecting the aqueous electrolyte into the first reservoir, at least one second reservoir extending into the silicon semiconductor substrate from the first main surface for holding an aqueous electrolyte, and a second groove for forming a salt bridge between the second reservoir and an exterior, said first and second reservoirs being formed by anisotropic etching of the silicon semiconductor substrate, the first reservoir extending from the first main surface of the silicon semiconductor substrate toward a second, opposite main surface of the silicon semiconductor substrate and the first reservoir having a sidewall defining an aperture at the second main surface of the silicon semiconductor substrate to expose the interior of the first reservoir, the aperture being disposed at a location corresponding to the position of the inside reference electrode embedded in the glass substrate; and
- a glass sensing film covering and sealing the aperture in the sidewall and thus at a position corresponding to said inside reference electrode.

10. A small glass electrode according to claim 9, wherein an electrolyte occupies the electrolyte-holding reservoir.

11. A small glass electrode according to claim 9, wherein the glass sensing film comprises two layers of glass film.

12. A small glass electrode according to claim 9, wherein said reference electrode is comprised of silver/silver chloride.

13. A small glass electrode according to claim 9, wherein said first and second pads and said first and second lead-in lines are made of gold or platinum.

14. A small glass electrode according to claim 9, wherein said semiconductor substrate is a (100) oriented silicon substrate.

15. A small glass electrode according to claim 9, further comprising a temperature sensor.

16. A small glass electrode according to claim 15, wherein said temperature sensor comprises a thin film resistor formed between the glass substrate and the silicon semiconductor substrate, said resistor being insulated from the inside and outside reference electrodes.

17. A small glass electrode combined with a temperature sensor, comprising a planar glass substrate and a silicon semiconductor substrate, the glass substrate having a first main surface and the silicon semiconductor substrate having first and second opposite main surfaces, the first main surfaces of the substrates being bonded to each other, the bonded substrates having a first portion for a glass electrode and a second portion for a temperature sensor, the first and second portions being separated from each other,
   i) said first portion comprising:
   - a reference electrode, a pad and a lead-in line, each embedded in the glass substrate, from the first main surface thereof, the lead-in line interconnecting said reference electrode and said pad;
   - at least one reservoir extending into the silicon semiconductor substrate from the first main surface of the silicon semiconductor substrate for holding an aqueous electrolyte, the reservoir having a sidewall defining an aperture at the second main surface of the silicon semiconductor substrate to expose the interior of the reservoir, the aperture being disposed at a location corresponding to the position of the reference electrode embedded in the glass substrate,
   - a groove forming a fluid passageway in communication with the reservoir for injecting the aqueous electrolyte into the reservoir, said groove and said reservoir being formed by anisotropic etching of the silicon semiconductor substrate, the reservoir extending from the first main surface toward the second main surface of the silicon semiconductor substrate; and
   - a glass sensing film covering and sealing the aperture in the sidewall and thus at a position corresponding to said reference electrode, and
   ii) said second portion comprising a thin film resistor formed between the bonded substrates.

18. A small glass electrode according to claim 17, wherein an electrolyte occupies the electrolyte-holding reservoir.

19. A small glass electrode according to claim 17, wherein the glass sensing film comprises two layers of glass film.

20. A small glass electrode according to claim 21, wherein said semiconductor substrate is a (100) oriented silicon substrate.

21. A small glass electrode according to claim 17, wherein said reference electrode is comprised of silver/silver chloride.

22. A small glass electrode according to claim 17, wherein said pad and said lead-in line are made of gold or platinum.

23. A small glass electrode according to claim 17, wherein the first portion further comprises an aqueous electrolyte solution held within said at least one reservoir.

* * * * *